US010529096B2

(12) United States Patent
Mak et al.

(10) Patent No.: US 10,529,096 B2
(45) Date of Patent: Jan. 7, 2020

(54) SYSTEM AND METHOD FOR CHARACTERIZING TISSUE ORGANIZATION USING POLARIZATION SENSITIVE OPTICAL COHERENCE TOMOGRAPHY

(71) Applicant: SYNAPTIVE MEDICAL (BARBADOS) INC., Bridgetown (BB)

(72) Inventors: Siu Wai Jacky Mak, Toronto (CA); Ho Yiu Kyle Cheng, Toronto (CA); Kai Michael Hynna, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 96 days.

(21) Appl. No.: 15/910,557

(22) Filed: Mar. 2, 2018

(65) Prior Publication Data
US 2019/0272652 A1    Sep. 5, 2019

(51) Int. Cl.
*G06K 9/00*    (2006.01)
*G06T 11/00*    (2006.01)
(Continued)

(52) U.S. Cl.
CPC .......... *G06T 11/006* (2013.01); *A61B 5/0042* (2013.01); *A61B 5/0066* (2013.01);
(Continued)

(58) Field of Classification Search
CPC ..... A61B 90/39; A61B 5/0042; A61B 5/0066; A61B 5/7257; A61B 5/7445; A61B 5/0073; A61B 3/102; A61B 2090/3937; A61B 2090/3983; A61B 2576/00; G06T 11/006; G06T 11/003; G06T 7/11; G06T 7/0012; G06T 7/12; G06T 7/149; G06T 2207/10101; G06T 2207/20056;
(Continued)

(56) References Cited

U.S. PATENT DOCUMENTS 7,289,225 B2 * 10/2007 De Groot .......... G01B 11/0675
356/497
7,782,464 B2   8/2010 Mujat et al.
(Continued)

FOREIGN PATENT DOCUMENTS

KR   20090021480 A   3/2009
KR   20090093368 A   9/2009

OTHER PUBLICATIONS

Sakai, Shingo, et al. "In vivo three-dimensional birefringence analysis shows collagen differences between young and old photo-aged human skin." Journal of Investigative Dermatology 128.7 (2008): 1641-1647.
(Continued)

Primary Examiner — Jose L Couso
(74) Attorney, Agent, or Firm — Perry + Currier, Inc.

(57) ABSTRACT

A system and method for characterizing tissue organization using polarization sensitive optical coherence (PSOCT) tomography is provided. A PSOCT device is controlled, by a computing device, to obtain PSOCT A-line scans across a sample. For each of the PSOCT A-line scans, the computing device determines a frequency characteristic of any banding present in a respective PSOCT A-line retardance scan. The computing device controls display device to render a map of the frequency characteristic.

20 Claims, 19 Drawing Sheets

(51) Int. Cl.
*G06T 7/11* (2017.01)
*A61B 5/00* (2006.01)
*A61B 90/00* (2016.01)
*G06T 7/00* (2017.01)

(52) U.S. Cl.
CPC .......... *A61B 5/7257* (2013.01); *A61B 5/7445* (2013.01); *A61B 90/39* (2016.02); *G06T 7/0012* (2013.01); *G06T 7/11* (2017.01); *A61B 2090/3937* (2016.02); *A61B 2090/3983* (2016.02); *G06T 2207/10101* (2013.01); *G06T 2207/20056* (2013.01); *G06T 2207/20064* (2013.01); *G06T 2207/30016* (2013.01); *G06T 2211/40* (2013.01)

(58) Field of Classification Search
CPC . G06T 2207/20064; G06T 2207/30016; G06T 2207/20116; G06T 2207/20052; G06T 2211/40; G06T 2211/424; G06T 2210/41; G01B 9/02091; G01B 9/02011; G01B 9/02; G01B 9/02004; G01B 9/02044; G01B 2290/70; G02B 27/28; G06K 9/52
See application file for complete search history.

(56) References Cited

U.S. PATENT DOCUMENTS

| | | |
|---|---|---|
| 2003/0220749 A1 | 11/2003 | Chen et al. |
| 2005/0280828 A1* | 12/2005 | Fitzgerald de Boer ................. G01B 9/02091 356/497 |
| 2006/0055936 A1* | 3/2006 | Yun .................. G01N 21/4795 356/479 |
| 2006/0244973 A1* | 11/2006 | Yun ....................... A61B 5/0059 356/511 |
| 2007/0252951 A1* | 11/2007 | Hammer ................. A61F 9/008 351/221 |
| 2010/0033730 A1* | 2/2010 | Kim .................... G01B 9/02004 356/479 |
| 2014/0073917 A1* | 3/2014 | Huang ................. A61B 5/0066 600/427 |
| 2015/0101411 A1* | 4/2015 | Zalev ................. G01N 29/2418 73/643 |
| 2015/0168214 A1* | 6/2015 | Wong ................. G01B 9/02004 356/402 |
| 2016/0206195 A1* | 7/2016 | Huang ................. A61B 3/0025 |
| 2016/0305762 A1 | 10/2016 | Suter et al. |
| 2017/0024910 A1* | 1/2017 | Griffin ................. G06T 11/003 |
| 2017/0120337 A1* | 5/2017 | Kanko ................. B22F 3/1055 |
| 2018/0271430 A1 | 9/2018 | Ramella-Roman |
| 2019/0117076 A1* | 4/2019 | Fan ....................... G06T 11/006 |

OTHER PUBLICATIONS

Ugryumova, Nadya, et al. "Novel optical imaging technique to determine the 3-D orientation of collagen fibers in cartilage: variable-incidence angle polarization-sensitive optical coherence tomography." Osteoarthritis and cartilage 17.1 (2009): 33-42.

Villiger, Martin, et al. "Deep tissue volume imaging of birefringence through fibre-optic needle probes for the delineation of breast tumour." Scientific reports 6 (2016): 28771.

Oldenbourg, Rudolf. "Analysis of edge birefringence." Biophysical journal 60.3 (1991): 629-641.

Sharma, Priyanka, et al. "Human ex-vivo oral tissue imaging using spectral domain polarization sensitive optical coherence tomogrpahy." Lasers in medical science 32.1 (2017): 143-150.

UKIPO, Search Report under Section 17, Aug. 6, 2019, re UK Patent Application No. GB1902832.3.

\* cited by examiner

- 125 points (125 to 250)
- Peak ~3.0-3.5 cycle/mm. Shorter peak than before, but still dominant.

SYSTEM AND METHOD FOR CHARACTERIZING TISSUE ORGANIZATION USING POLARIZATION SENSITIVE OPTICAL COHERENCE TOMOGRAPHY

FIELD

The specification relates generally to polarization sensitive optical coherence tomography and specifically to a system and method for characterizing tissue organization using polarization sensitive optical coherence tomography.

BACKGROUND

There is a lack of quantitative tools for evaluating and comparing tissue organization on tissue, particularly on unprocessed tissue (e.g. non-frozen tissue, non-fixed tissue and/or tissue not conjugated with a fluorochrome reagent and the like). Furthermore, there is a lack of such quantitative tools that are usable intra-operatively, for example in an operating room. Tissue organization may be assessed qualitatively in a subjective way, for example, by visually observing tissue, with a trained eye, to determine if the tissue looks organized. While there are some imaging methods, such as second and third harmonic imaging that, image collagen content in a piece of tissue, such methods may be qualitative, slow and may only be performed on exercised tissue; such methods may also require large and expensive equipment to perform the imaging. MiCASA (Multitaper Circularly Average Spectrum Analysis) is another recently developed technique that quantifies tissue organization at the cellular level through spatial correlation functions of fluorescence images from tissue conjugated with a fluorochrome regent; unfortunately, this method can only be done also on exercised tissue, and tissue processing is required to conjugate a fluorochrome regent onto the tissue for imaging.

SUMMARY

The present disclosure is generally directed to a system and method for characterizing tissue organization using polarization sensitive optical coherence tomography (PSOCT) that may be used in-vivo (e.g. in an operating room) and/or in-vitro; in other words, with live tissue and/or with excised tissue. PSOCT A-line scans are performed on the tissue using a polarization sensitive optical coherence tomography device and a frequency characteristic of any banding in PSOCT A-line retardance scans are determined. A display device may be controlled to render a map of the frequency characteristic. The banding in a PSOCT A-line scan is generally indicative of organization in tissue, and hence a frequency characteristic of a PSOCT A-line scan is also generally indicative of organization in tissue. Such frequency characteristics may include, but are not limited to, slope of one or more of the bands, including rising and falling slopes, a dominant frequency of a Fourier Transform of one or more of the PSOCT A-line retardance scans and/or a highest Fourier Transform coefficient of a Fourier Transform of one or more of the PSOCT A-line retardance scans, a dominant frequency determined from a wavelet transform of one or more of the PSOCT A-line retardance scans, and the like. Furthermore, by selecting bands to analyze according to depth, tissue organization may be characterized according to depth. As PSOCT is generally compatible with both in-vivo and in-vitro tissue, and as the techniques described herein do not rely on any special tissue processing (e.g. such as conjugation with a fluorochrome reagent), the techniques described herein are generally compatible with both in-vivo and in-vitro tissue.

Hence, the techniques described herein are generally compatible with image guided medical procedures using an access port. This port-based surgery approach allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. The techniques described herein may assist a surgeon performing brain surgery, and the like, via an access port in determining locations of organized tissue in a brain.

An aspect of the specification provides a system comprising: a polarization sensitive optical coherence tomography (PSOCT) device; a display device; and a computing device configured to: control the PSOCT device to obtain PSOCT A-line scans across a sample; for each of the PSOCT A-line scans, determine a frequency characteristic of any banding present in a respective PSOCT A-line retardance scan; and control the display device to render a map of the frequency characteristic.

Another aspect of the specification provides a method comprising: controlling, at a computing device, a polarization sensitive optical coherence tomography (PSOCT) device to obtain PSOCT A-line scans across a sample; for each of the PSOCT A-line scans, determining, at the computing device, a frequency characteristic of any banding present in a respective PSOCT A-line retardance scan; and controlling, at a computing device, a display device to render a map of the frequency characteristic.

BRIEF DESCRIPTIONS OF THE DRAWINGS

For a better understanding of the various implementations described herein and to show more clearly how they may be carried into effect, reference will now be made, by way of example only, to the accompanying drawings in which.

DETAILED DESCRIPTION

Figure 1:
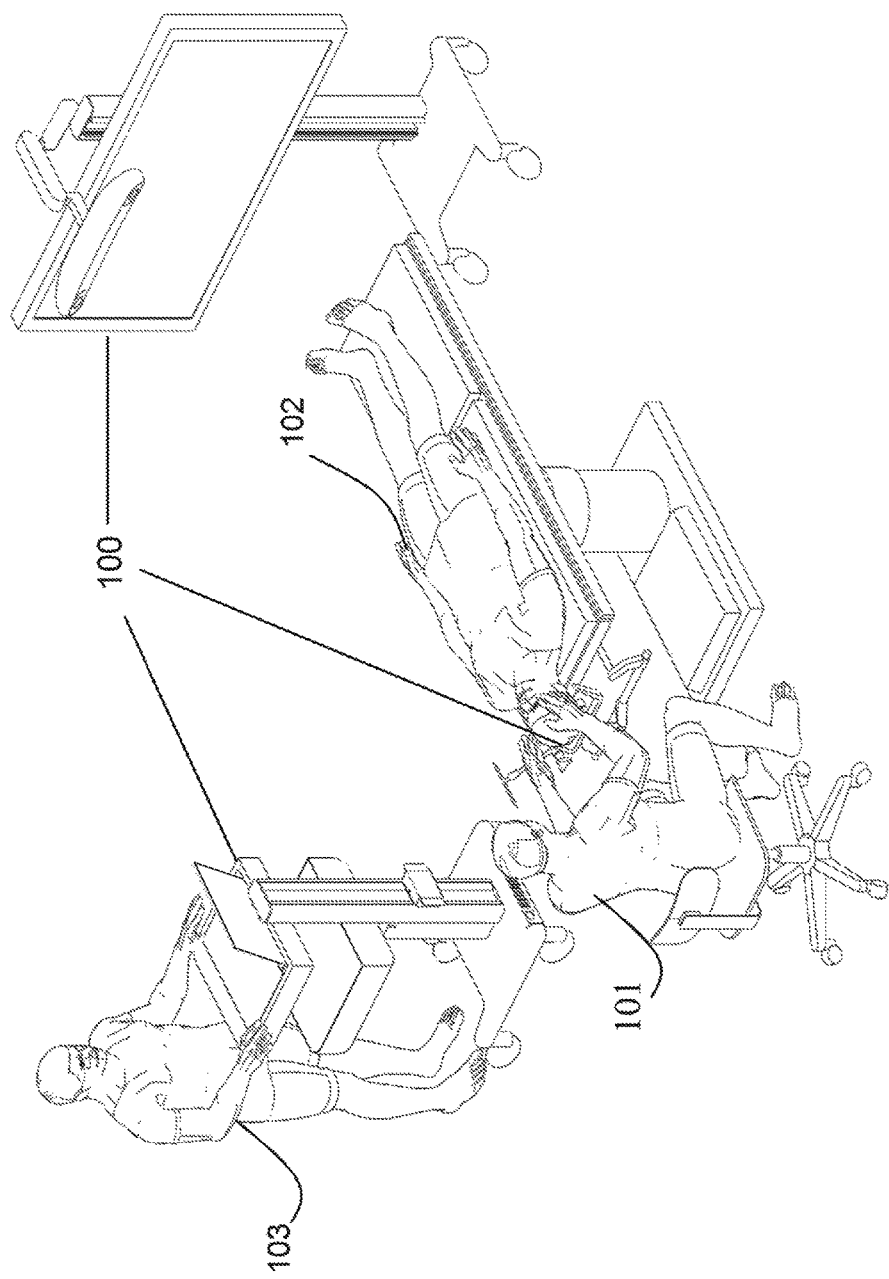
FIG. 1 shows an example operating room setup for a minimally invasive access port-based medical procedure, according to non-limiting implementations.

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

The systems and methods described herein may be useful in the field of neurosurgery, including oncological care, neurodegenerative disease, stroke, brain trauma and orthopedic surgery; however, persons of skill will appreciate the ability to extend these concepts to other conditions or fields of medicine. It should be noted that the surgical process is applicable to surgical procedures for brain, spine, knee and any other suitable region of the body.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

The terms "about", "substantially", "essentially", "approximately", and the like, are defined as being "close to", for example as understood by persons of skill in the art. In some implementations, the terms are understood to be "within 10%," in other implementations, "within 5%", in yet further implementations, "within 1%", and in yet further implementations "within 0.5%".

Referring to FIG. 1, a non-limiting example navigation system 100 is shown to support minimally invasive access port-based surgery. In FIG. 1, a neurosurgeon 101 conducts a minimally invasive port-based surgery on a patient 102 in an operating room (OR) environment. The navigation system 100 includes an equipment tower, tracking system, displays and tracked instruments to assist the surgeon 101 during the procedure. An operator 103 may also be present to operate, control and provide assistance for the navigation system 100.

Figure 2:
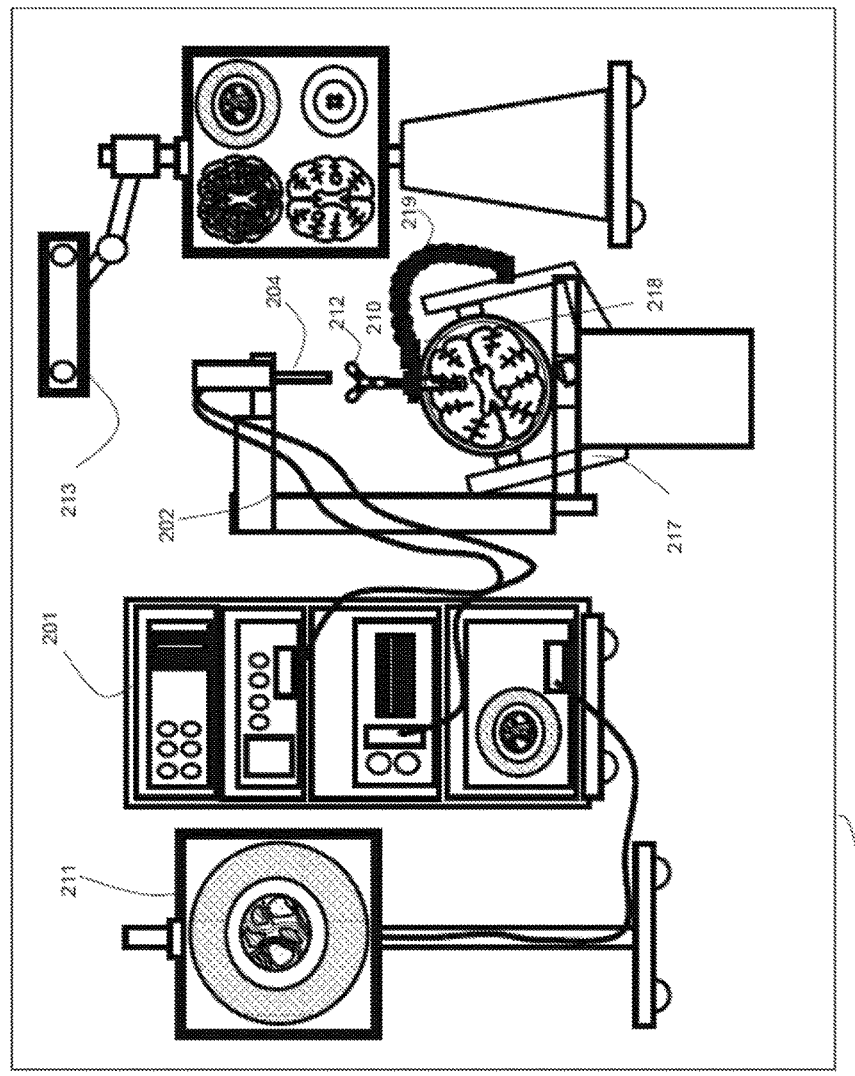
FIG. 2 is a block diagram illustrating components of a medical navigation system that may be used to implement a surgical plan for a minimally invasive surgical procedure, according to non-limiting implementations.

Referring to FIG. 2, a block diagram is shown illustrating components of an example medical navigation system 200, according to non-limiting implementations. The medical navigation system 200 illustrates a context in which a surgical plan including equipment (e.g., tool and material)

tracking, such as that described herein, may be implemented. The medical navigation system 200 includes, but is not limited to, one or more monitors 205, 211 for displaying a video image, an equipment tower 201, and a mechanical arm 202, which supports an optical scope 204. The equipment tower 201 may be mounted on a frame (e.g., a rack or cart) and may contain a computer or controller (examples provided with reference to FIGS. 3 and 6 below), planning software, navigation software, a power supply and software to manage the mechanical arm 202, and tracked instruments. In one example non-limiting implementation, the equipment tower 201 may comprise a single tower configuration with dual display monitors 211, 205, however other configurations may also exist (e.g., dual tower, single display, etc.). Furthermore, the equipment tower 201 may also be configured with a universal power supply (UPS) to provide for emergency power, in addition to a regular AC adapter power supply.

A patient's anatomy may be held in place by a holder. For example, in a neurosurgical procedure the patient's head may be held in place by a head holder 217, and an access port 206 and an introducer 210 may be inserted into the patient's head. The introducer 210 may be tracked using a tracking camera 213, which provides position information for the navigation system 200. The tracking camera 213 may also be used to track tools and/or materials used in the surgery, as described in more detail below. In one example non-limiting implementation, the tracking camera 213 may comprise a 3D (three-dimensional) optical tracking stereo camera, similar to one made by Northern Digital Imaging (NDI), configured to locate reflective sphere tracking markers 212 in 3D space. In another example, the tracking camera 213 may comprise a magnetic camera, such as a field transmitter, where receiver coils are used to locate objects in 3D space, as is also known in the art. Location data of the mechanical arm 202 and access port 206 may be determined by the tracking camera 213 by detection of tracking markers 212 placed on these tools, for example the introducer 210 and associated pointing tools. Tracking markers may also be placed on surgical tools or materials to be tracked. The secondary display 205 may provide output of the tracking camera 213. In one example non-limiting implementation, the output may be shown in axial, sagittal and coronal views as part of a multi-view display.

As noted above with reference to FIG. 2, the introducer 210 may include tracking markers 212 for tracking. The tracking markers 212 may comprise reflective spheres in the case of an optical tracking system and/or pick-up coils in the case of an electromagnetic tracking system. The tracking markers 212 may be detected by the tracking camera 213 and their respective positions are inferred by the tracking software.

As shown in FIG. 2, a guide clamp 218 (or more generally a guide) for holding the access port 206 may be provided. The guide clamp 218 may optionally engage and disengage with the access port 206 without needing to remove the access port 206 from the patient. In some examples, the access port 206 may be moveable relative to the guide clamp 218, while in the guide clamp 218. For example, the access port 206 may be able to slide up and down (e.g., along the longitudinal axis of the access port 206) relative to the guide clamp 218 while the guide clamp 218 is in a closed position. A locking mechanism may be attached to or integrated with the guide clamp 218, and may optionally be actuatable with one hand, as described further below. Furthermore, an articulated arm 219 may be provided to hold the guide clamp 218. The articulated arm 219 may have up to six degrees of freedom to position the guide clamp 218. The articulated arm 219 may be lockable to fix its position and orientation, once a desired position is achieved. The articulated arm 219 may be attached or attachable to a point based on the patient head holder 217, or another suitable point (e.g., on another patient support, such as on the surgical bed), to ensure that when locked in place, the guide clamp 218 does not move relative to the patient's head.

Figure 3:
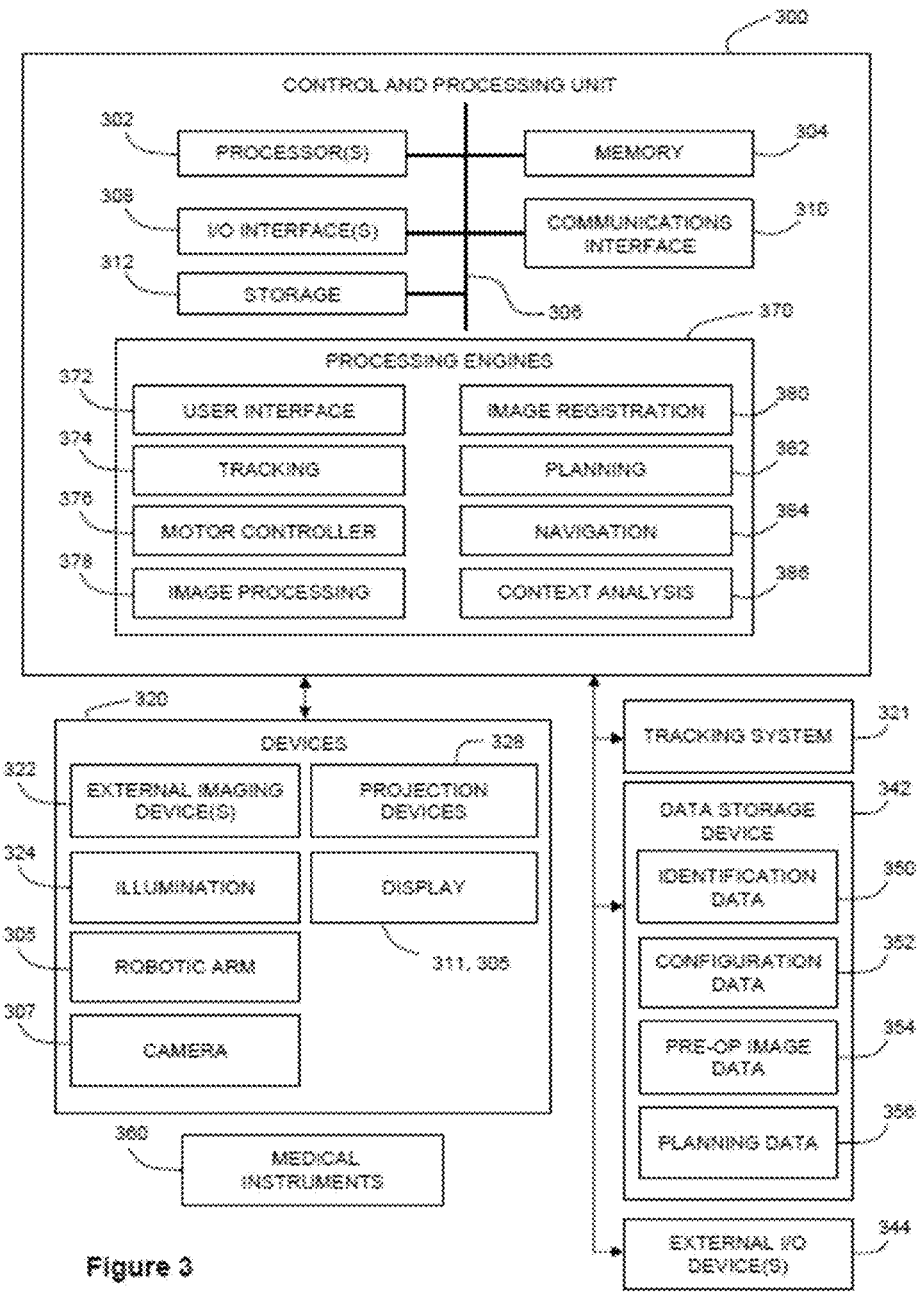
FIG. 3 depicts a block diagram illustrating components of a planning system used to plan a medical procedure that may then be implemented using the navigation system of FIG. 2, according to non-limiting implementations.

Referring to FIG. 3, a block diagram is shown illustrating a control and processing unit 300 that may be used in the navigation system 200 of FIG. 2 (e.g., as part of the equipment tower). In one example non-limiting implementation, control and processing unit 300 may include one or more processors 302, a memory 304, a system bus 306, one or more input/output interfaces 308, a communications interface 310, and storage device 312. In particular, one or more processors 302 may comprise one or more hardware processors and/or one or more microprocessors. Control and processing unit 300 may be interfaced with other external devices, such as tracking system 321, data storage device 342, and external user input and output devices 344, which may include, but is not limited to, one or more of a display, keyboard, mouse, foot pedal, and microphone and speaker. Data storage device 342 may comprise any suitable data storage device, including, but not limited to a local and/or remote computing device (e.g. a computer, hard drive, digital media device, and/or server) having a database stored thereon. In the example shown in FIG. 3, data storage device 342 includes, but is not limited to, identification data 350 for identifying one or more medical instruments 360 and configuration data 352 that associates customized configuration parameters with one or more medical instruments 360. Data storage device 342 may also include, but is not limited to, preoperative image data 354 and/or medical procedure planning data 356. Although data storage device 342 is shown as a single device in FIG. 3, in other implementations, data storage device 342 may be provided as multiple storage devices.

Medical instruments 360 may be identifiable using control and processing unit 300. Medical instruments 360 may be connected to and controlled by control and processing unit 300, and/or medical instruments 360 may be operated and/or otherwise employed independent of control and processing unit 300. Tracking system 321 may be employed to track one or more of medical instruments 360 and spatially register the one or more tracked medical instruments 360 to an intraoperative reference frame. In another example, a sheath may be placed over a medical instrument 360 and the sheath may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include, but are not limited, one or more external imaging devices 322, one or more illumination devices 324, a robotic arm 399, one or more projection devices 328, and one or more displays 305, 311.

Aspects of the specification may be implemented via processor(s) 302 and/or memory 304. For example, the functionalities described herein may be partially implemented via hardware logic in processor 302 and partially using the instructions stored in memory 304, as one or more processing modules 370 and/or processing engines. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example non-limiting implementation the processing modules 370 may be stored in the memory 304 and the processing modules may be collectively referred to as processing modules 370.

It is to be understood that the system is not intended to be limited to the components shown in FIG. 3. One or more components of the control and processing unit 300 may be provided as an external component or device. In one example non-limiting implementation, navigation engine 384 may be provided as an external navigation system that is integrated with control and processing unit 300.

Some implementations may be implemented using processor 302 without additional instructions stored in memory 304. Some implementations may be implemented using the instructions stored in memory 304 for execution by one or more general purpose microprocessors. Thus, the specification is not limited to a specific configuration of hardware and/or software.

While some implementations may be implemented in fully functioning computers and computer systems, various implementations are capable of being distributed as a computing product in a variety of forms and are capable of being applied regardless of the particular type of machine or computer readable media used to actually effect the distribution.

At least some aspects disclosed may be embodied, at least in part, in software. That is, the techniques may be carried out in a computer system or other data processing system in response to its processor, such as a microprocessor, executing sequences of instructions contained in a memory, such as read only memory (ROM), volatile random access memory (RAM), non-volatile memory, cache and/or a remote storage device.

A computer readable storage medium, and/or a non-transitory computer readable storage medium, may be used to store software and data which, when executed by a data processing system, causes the system to perform various methods. The executable software and data may be stored in various places including for example ROM, volatile RAM, non-volatile memory and/or cache. Portions of this software and/or data may be stored in any one of these storage devices.

Examples of computer-readable storage media include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical and/or other forms of propagated signals, such as carrier waves, infrared signals, digital signals, and the like. The storage medium may comprise the internet cloud, storage media therein, and/or a computer readable storage medium and/or a non-transitory computer readable storage medium, including, but not limited to, a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB (Universal Serial Bus) keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 200, which may include control and processing unit 300, is to provide tools to a surgeon and/or a neurosurgeon that will lead to the most informed, least damaging neurosurgical operations. In addition to removal of brain tumours and intracranial hemorrhages (ICH), the navigation system 200 may also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present specification may be applied to other suitable medical procedures.

Figure 4:
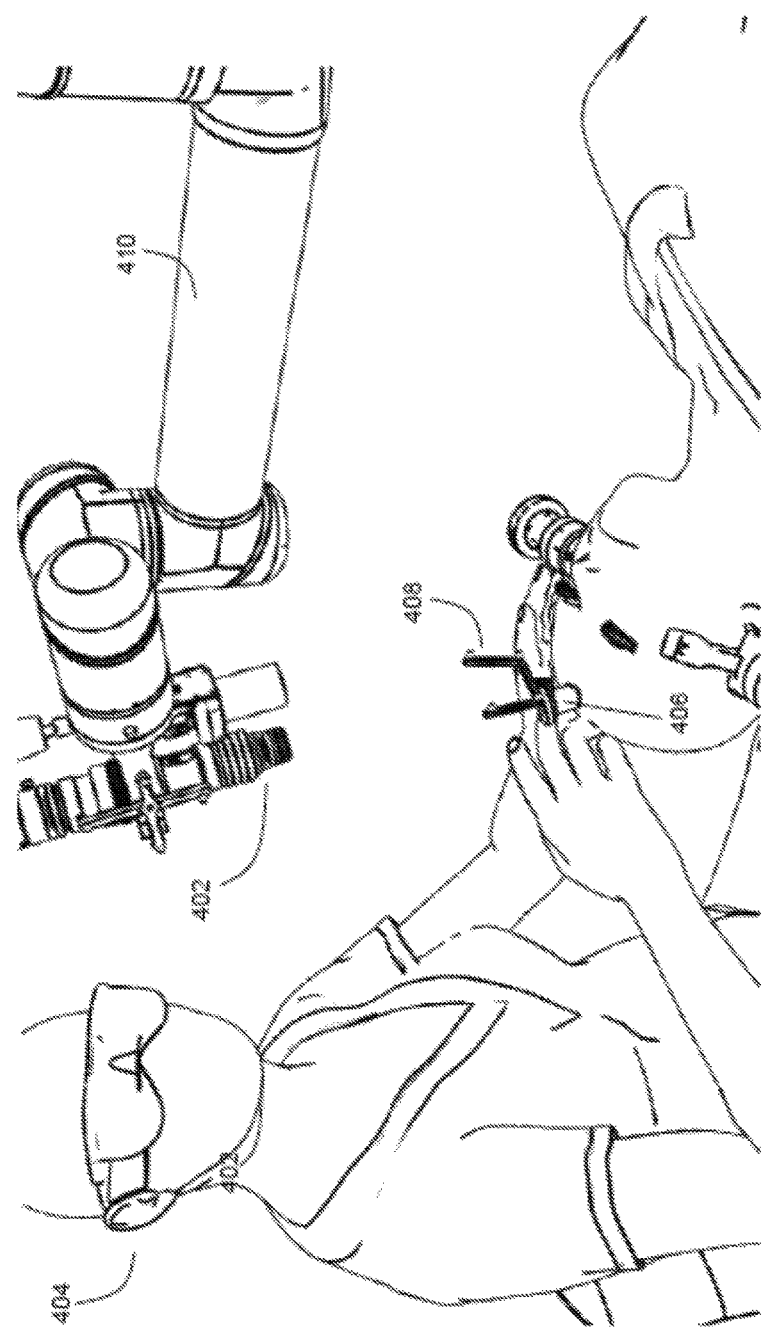
FIG. 4 depicts an example implementation port based brain surgery using a video scope, according to non-limiting implementations.

Attention is next directed to FIG. 4 which depicts a non-limiting example of a port-based brain surgery procedure using a video scope. In FIG. 4, operator 404, for example a surgeon, may align video scope 402 to peer down port 406. Video scope 402 may be attached to an adjustable mechanical arm 410. Port 406 may have a tracking tool 408 attached to it where tracking tool 408 is tracked by a tracking camera of a navigation system.

Even though the video scope 402 may comprise an endoscope and/or a microscope, these devices introduce optical and ergonomic limitations when the surgical procedure is conducted over a confined space and conducted over a prolonged period such as the case with minimally invasive brain surgery.

Figure 5:
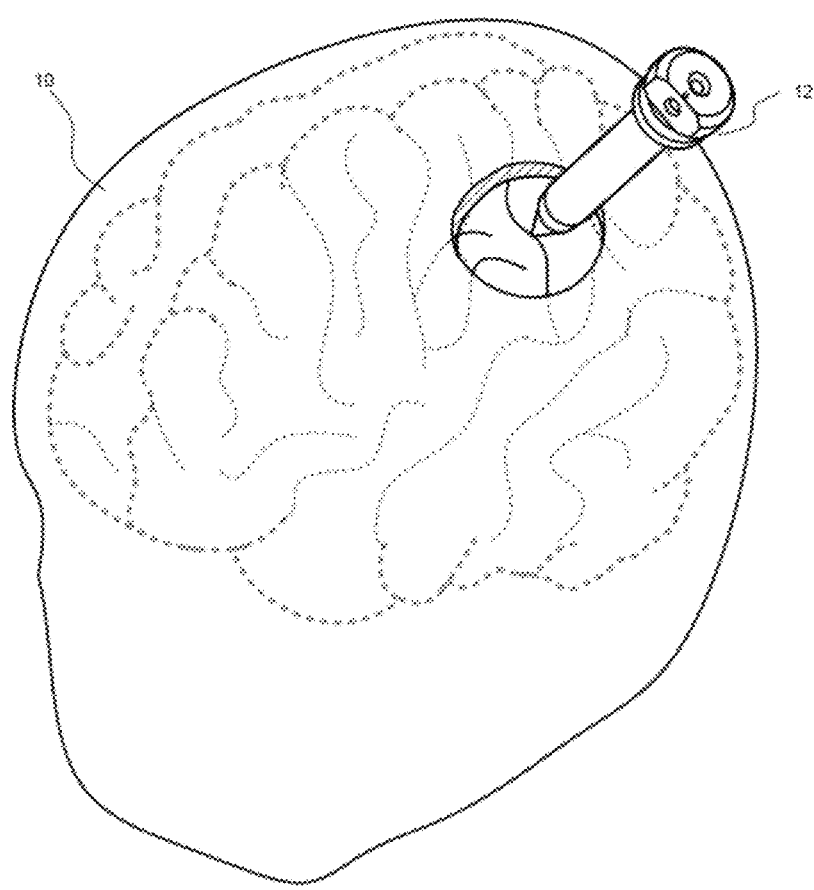
FIG. 5 depicts insertion of an access port into a human brain, for providing access to interior brain tissue during a medical procedure, according to non-limiting implementations.

FIG. 5 illustrates the insertion of an access port 12 into a human brain 10, in order to provide access to interior brain tissue during a medical procedure. In FIG. 5, access port 12 is inserted into a human brain 10, providing access to interior brain tissue. Access port 12 may include, but is not limited to, instruments such as catheters, surgical probes, and/or cylindrical ports such as the NICO BrainPath. Surgical tools and instruments may then be inserted within a lumen of the access port 12 in order to perform surgical, diagnostic or therapeutic procedures, such as resecting tumors as necessary. However, the present specification applies equally well to catheters, DBS needles, a biopsy procedure, and also to biopsies and/or catheters in other medical procedures performed on other parts of the body.

In the example of a port-based surgery, a straight and/or linear access port 12 is typically guided down a sulci path of the brain. Surgical instruments and/or surgical tools would then be inserted down the access port 12.

Figure 6:
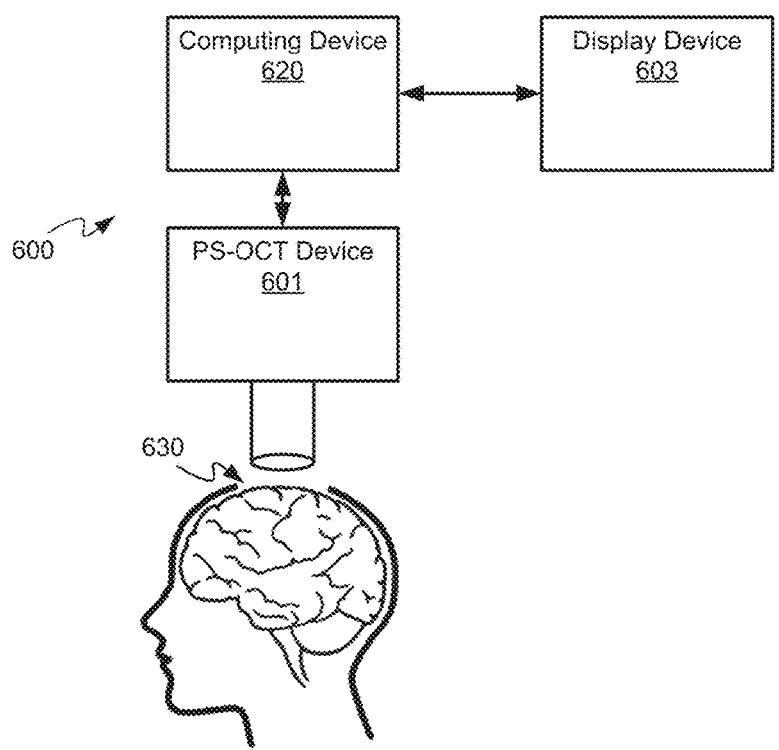
FIG. 6 depicts a system for characterizing tissue organization using polarization sensitive optical coherence tomography, according to non-limiting implementations.

Attention is next directed to FIG. 6, which depicts an example of a system and method for characterizing tissue organization using polarization sensitive optical coherence tomography system that includes a polarization sensitive optical coherence tomography that could be used with the access port 12 and/or in open case surgery.

Specifically, FIG. 6 depicts a system 600 comprising: polarization sensitive optical coherence tomography (PSOCT) device 601; a display device 603; and a computing device 620. As depicted, the PSOCT device is being used with a sample 630, as depicted a human brain (such as human brain 10), in-vivo, for example via an access port (not depicted). The computing device 620 is configured to: control the PSOCT device 601 to obtain PSOCT A-line scans across a sample (e.g. the sample 630); for each of the PSOCT A-line scans, determine a frequency characteristic of any banding present in a respective PSOCT A-line retardance scan; and control the display device 611 to render a map of the frequency characteristic. As such, the computing device 620 can be a component, for example, of the control and processing unit 300. Furthermore, while the system 600 is shown in use with an in-vivo sample, the system 600 may also be used with an in-vitro sample.

While details of the PSOCT device 601 are not depicted, it is assumed that PSOCT device 601 is generally configured for PSOCT scanning and hence includes a PSOCT interferometer, a scanning device (e.g. to scan across the sample 630), and any other components used for PSOCT scanning. The PSOCT device 601 generally acquires PSOCT A-line scans of a sample; an PSOCT A-line scan or an "axial-line scans" is generally an PSOCT scan into a sample, for example along an axis into the sample, such as a normal axis, and the like, though A-line scans may also be acquired at non-normal angles. When a plurality of PSOCT A-line scans are performed laterally across the sample, the PSOCT A-line scans may be combined into a PSOCT B-scan (e.g. a two-dimensional cross-sectional image) of the portion of the sample over which the PSOCT A-line scans occurred. When a plurality of PSOCT B-line scans are performed laterally across an area of a sample, the PSOCT B-line scans may be combined into a partial three-dimensional PSOCT image of the area of the sample over which the PSOCT A-line scans occurred.

The PSOCT device 601 may be controlled to scan the sample 630 using polarized OCT light in a PSOCT A-line scan. Two orthogonal polarization signals are reflected from the sample and detected by sensors, for example in individual channels. The intensity of the individual channels is combined to generate an OCT A-line intensity scan. The arctan of the intensity ratio between the two polarization components represented by the individual channels is used to generate an OCT A-line retardation scan. Alternatively, A-line retardation can be calculated from Stokes parameters (i.e. parameters calculated from intensity reflections) of multiple different input polarizations.

The PSOCT A-line scans, may include banding. In particular, banding in PSOCT A-line retardance scans are generally indicative of tissue organization in a sample. Furthermore, the banding may be depth dependent with bands at different depths having different shapes and/or frequency characteristics. Hence, any depth dependency of the banding may also be indicative of depth dependency of tissue organization.

As optical coherence tomography enables imaging of tissue to depths of typically 1-2 mm (e.g. due to the light absorption and scattering property of tissue), the system 600, including the PSOCT device 601 may be used to determine tissue organization to depths up to about 2 mm. However, the depth to which light from the PSOCT device 601 penetrates a sample may depend on the light absorption and scattering properties of the sample; hence the system 600 may be used to determine tissue organization to depths less than about 1 mm and greater than about 2 mm Furthermore, the PSOCT device 601 is generally configured to acquire en-face images of an area of the sample 630. In other words, intensity measurements of OCT light reflected from the surface of the sample 630 over an area being scanned may be used to generate an image of the sample which, when generated from OCT light, is also referred to as an en-face image. Alternatively, the system 600 may further comprise a camera (e.g. the video scope 402), and the like, configured to acquire images of the same region of the sample 630 being scanned by the PSOCT device 601.

The PSOCT device 601 may comprise a handheld device or a non-handheld device. For example, the PSOCT device 601 comprise a housing configured to be held by a human hand. Alternatively, the PSOCT device 601 may be mounted to a surgical arm, and the like, such as the arms 219, 410. Furthermore, the PSOCT device 601 may be integrated with a camera, such as the video scope 402, and mounted to a surgical arm, and the like. The PSOCT device 601 may further comprise an endoscope device or a non-endoscope device. For example, the PSOCT device 601 may comprise a small flexible and sterile housing configured to be inserted into the human body.

Figure 7:
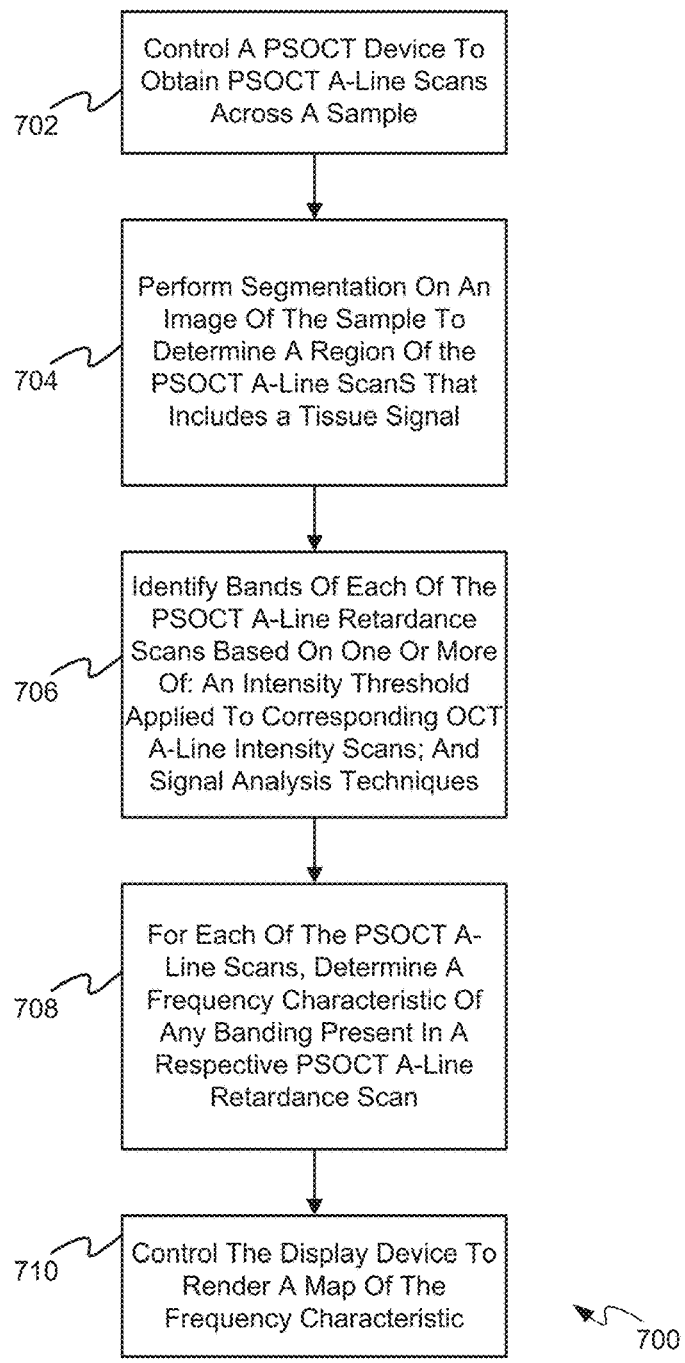
FIG. 7 depicts a method for characterizing tissue organization using polarization sensitive optical coherence tomography, according to non-limiting implementations.

Attention is now directed to FIG. 7, which depicts a flowchart of a method 700 for method for characterizing tissue organization using polarization sensitive optical coherence tomography using the system 600, according to non-limiting implementations. In order to assist in the explanation of the method 700, it will be assumed that the method 700 is performed using the computing device 620. Indeed, the method 700 is one way in which the computing device 620 and/or the system 600 can be configured. Furthermore, the following discussion of the method 700 will lead to a further understanding of the system 600 and its various components. However, it is to be understood that the system 600 and/or the method 700 can be varied, and need not work exactly as discussed herein in conjunction with each other, and that such variations are within the scope of present implementations.

Regardless, it is to be emphasized, that the method 700 need not be performed in the exact sequence as shown, unless otherwise indicated; and likewise, various blocks may be performed in parallel rather than in sequence; hence the elements of the method 700 are referred to herein as "blocks" rather than "steps". It is also to be understood, however, that the method 700 can be implemented on variations of the system 600 and/or the computing device 620 as well. Furthermore, while the computing device 620 is described as implementing and/or performing each block of the method 700, it is appreciated that one or more blocks of the method 700 occurs in conjunction with the PSOCT device 601 and the display device 603.

At a block 702, the computing device 620 controls the PSOCT device to obtain PSOCT A-line scans across a sample, for example in acquisition of an image of the sample.

At an optional block 704, the computing device 620 performs segmentation on the image to determine a region of the PSOCT A-line scans that includes a tissue signal (i.e. from the surface of the tissue of the sample to a depth of the PSOCT A-line scans to which light penetrated) Such segmentation may reduce processing resources at the computing device 620 when determining a frequency characteristic of any banding present in the respective PSOCT A-line retardance scan. Alternatively, an intensity threshold applied to corresponding OCT A-line intensity scans could also be used to determine the surface of the sample in the PSOCT A-line retardance scan. In another embodiment, a conventional surface segmentation technique utilizing a PSOCT B-scan or PSOCT 3D scan could be performed.

At block 706, the computing device 620 identifies bands of each of the PSOCT A-line retardance scans for analysis based on one or more of: an intensity threshold applied to corresponding OCT A-line intensity scans; and signal analysis techniques. When the computing device 620 performs the block 704, identification of bands may be performed only on those portions of the PSOCT A-line scans that have been identified as being below the surface of the sample. Furthermore, the block 706 may be optional, for example when Fourier Transforms and/or wavelet transforms, and the like, are used to determine a frequency characteristic. As described in more detail below, the frequency characteristic may be determined as a function of depth.

At a block 708, the computing device 620, for each of the PSOCT A-line scans, determines a frequency characteristic of any banding present in a respective PSOCT A-line retardance scan. In some embodiments, the blocks 704, 706, 708 may be combined into one block such that segmentation (when performed), band identification and frequency characteristic determination occur in parallel and/or in conjunction with each other.

Such frequency characteristics may include, but are not limited to: a rising slope of a band in the respective PSOCT A-line retardance scan; a falling slope of the band in the respective PSOCT A-line retardance scan; an average of rising slopes of two or more bands in the respective PSOCT A-line retardance scan; an average of fallings slopes of the two or more bands in the respective PSOCT A-line retardance scan; and an average of a of the rising slopes and the falling slopes of the two or more bands in the respective PSOCT A-line retardance scan. Similarly, such frequency characteristics may also include, but are not limited to: a slope of one or more of bands in the respective PSOCT A-line retardance scan multiplied by a number of the bands used to determine the slope. Similarly, such frequency characteristics may also include, but are not limited to: a dominant frequency determined from a Fourier Transform of the respective PSOCT A-line retardance scan; and a Fourier Transform coefficient of the dominant frequency of the Fourier Transform of the respective PSOCT A-line retardance scan, the Fourier Transform coefficient of the dominant frequency being a highest Fourier Transform coefficient of a plurality of Fourier Transform coefficients. Similarly, such frequency characteristics may also include, but are not limited to: a dominant frequency determined from a wavelet transform of bands in the respective PSOCT A-line retardance scan. However, any type of frequency characteristic that characterizes the bands of PSOCT A-line retardance scan are within the scope of present embodiments.

At block 710, the computing device 620 controls the display device 603 to render a map of the frequency characteristic. While more than one frequency characteristic may be determined, generally only one frequency characteristic is mapped at the block 710. When more than one frequency characteristic is determined, the frequency characteristic that is mapped at the block 710 may be selected using a menu system, and the like, at the computing device 620 (e.g. using an input device and/or an I/O interface 308 of the control and processing unit 300).

Furthermore, the frequency characteristic may be determined as function of depth in the sample, and at the block 710 the computing device may control the display device 603 to render the map of the frequency characteristic according to the depth, for example a depth selected at the computing device 620 via a menu system, and the like.

In some embodiments, the computing device 620 may control the PSOCT device 601 to obtain one or more of an image and an en-face image of the sample, for example by assembling intensity measurements in OCT A-line intensity scans across the sample into an en-face image. In these embodiments, at the block 710, the computing device 620 may control the display device 603 to render the map of the frequency characteristic on one or more of the image and the en-face image. In some of these embodiments, the computing device 620 may control the PSOCT device to obtain one or more images corresponding to different depths of the sample (e.g. using intensity of the OCT A-line intensity scans at a given depth), and at the block 710 the computing device 620 may control the display device 603 to render the map of the frequency characteristic on the one or more images according to depth, for example the same depth at which an image is obtained, and onto which the map of the frequency characteristic is being rendered.

However, the computing device 620 may alternatively acquire an image from a camera (such as video scope 402) and at the block 710 the computing device 620 may control the display device 603 to render the map of the frequency characteristic on the image acquired by the camera.

Example embodiments of the method 700 are now described with respect to FIG. 8 to FIG. 19.

Figure 8:
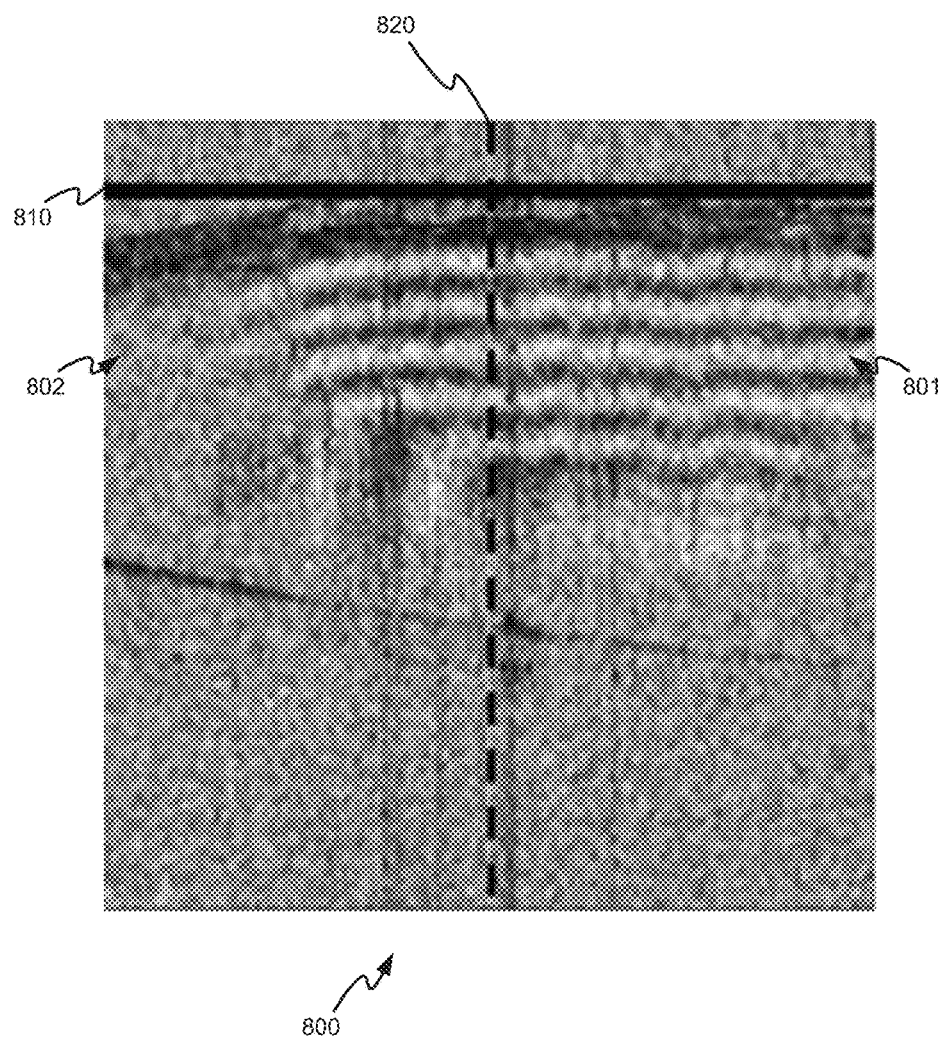
FIG. 8 depicts a PSOCT B-line scan of a sample, according to non-limiting implementations.

Attention is next directed to FIG. 8 which depicts a PSOCT B-line scan 800 of a sample, such as the sample 630. The PSOCT B-line scan 800 is depicted to provide an example of banding that occurs in organized tissue. For example, the PSOCT B-line scan 800 includes several regions including: a region 801 that includes bands and a region 802 that does not include bands. As such, tissue organization in the region 801 is higher than in the region 802. In general, tissue organization refers to structure, and the like, within tissue; hence, the region 801 includes more structure than the regions 802. For example, the region 802 may be generally amorphous, while the region 801 may include structural features such as bone, structured tissue, and the like.

Also depicted in the PSOCT B-line scan 800 is a line 810 which indicates a surface of the tissue, as well as a line 821 corresponding to an PSOCT A-line scan that occurred when performing the PSOCT B-line scan 800.

In other words, it is assumed in FIG. 8 that the computing device 620 has implemented the block 702 to acquire PSOCT A-line scans, which have then been combined into the an PSOCT B-line scan 800, one of the PSOCT A-line scans corresponding to the line 821. It is further assumed in FIG. 8 that the computing device 620 has implemented the block 704 to performed segmentation on one or more of each of the PSOCT A-line retardance scans and corresponding OCT A-line intensity scans to determine a surface of the sample that was scanned as indicated by the line 820.

Figure 9:
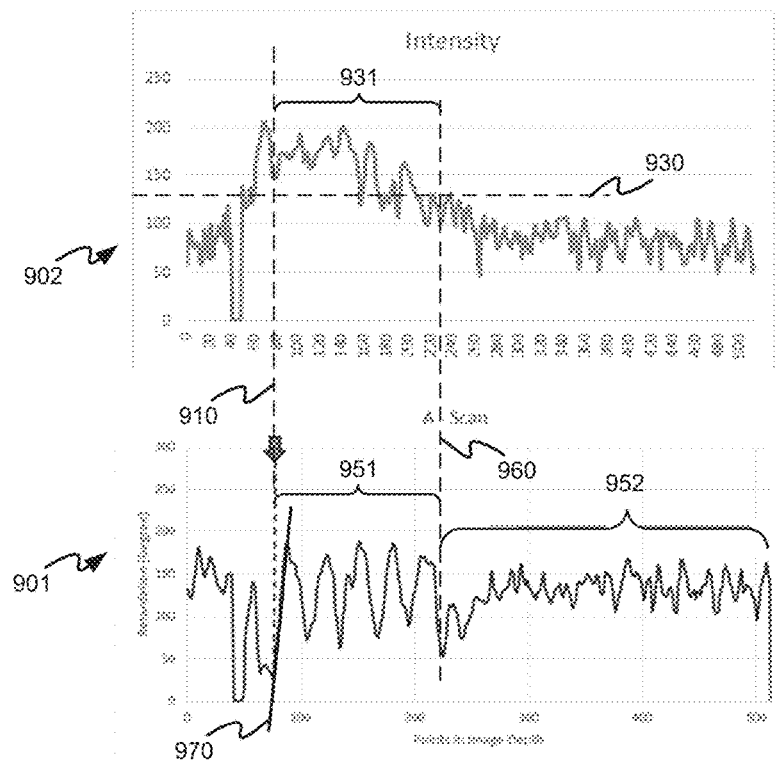
FIG. 9 depicts a PSOCT A-line retardance scan and a OCT A-line intensity scan, each derived from the PSOCT A-line scan of FIG. 8, along a line of the PSOCT A-line scan of FIG. 8, and in which in which a rising slope of a first band of PSOCT A-line retardance scan has been determined, according to non-limiting implementations.
Figure 10:
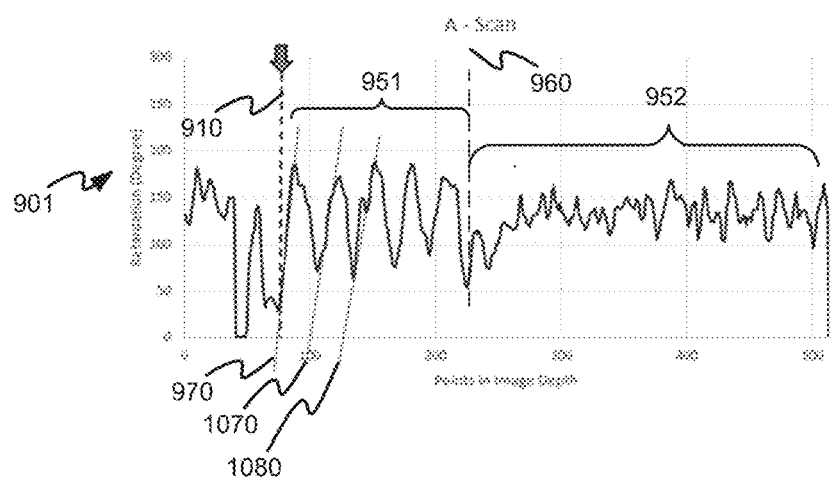
FIG. 10 depicts the PSOCT A-line retardance scan of FIG. 9 in which rising slopes of each of the first band, a second band and a third band has been determined, according to non-limiting implementations.

Attention is next directed to FIG. 9 which depicts a PSOCT A-line retardance scan 901 and a OCT A-line intensity scan 902, each derived from the PSOCT A-line scan along the line 820 of the PSOCT B-line scan 800. It is assumed that the PSOCT A-line retardance scan 901 and the OCT A-line intensity scan 902 have been acquired by the computing device 620 and that the computing device 620 is processing the PSOCT A-line retardance scan 901 and the OCT A-line intensity scan 902, for example while implementing the method 700.

Indeed, the PSOCT A-line retardance scan 901 and the OCT A-line intensity scan 902 may be acquired as the PSOCT B-line scan 800 is acquired. As depicted, each of the scans 901, 902 have an x-axis of "points in image depth" which corresponds to a depth into a sample, for example the sample 630. As depicted, the x-axes of the scan 901, 902 are aligned. The y-axis of the scan 901 indicates retardation in degrees, and the y-axis of the scan 902 indicates intensity in arbitrary units.

The scans 901, 902 are further depicted with a line 910 that corresponds to tissue surface in the PSOCT B-line scan.

Hence, segmentation has occurred at the block 704 of the method 700. Such segmentation may occur via analysis of the PSOCT B-line scan 800 and/or one or more of the PSOCT A-line retardance scan 901 and the corresponding OCT A-line intensity scan 902.

The OCT A-line intensity scan 902 is also depicted with a line 930 which represents a threshold intensity. The threshold intensity is selected such that a portion 931 of the OCT A-line intensity scan 902 above the threshold intensity (and in the sample as indicated by the line 910), may indicate a portion of the sample that are measurable using optical coherence tomography; in other words, when the intensity of the OCT A-line intensity scan 902 decreases to values that are less than the threshold intensity, as represented by the line 930, accurate OCT measurements may no longer be possible. The portion 931 is assumed to begin at the surface of the sample that was scanned, and hence the portion 931 begins at the line 910.

As depicted, the PSOCT A-line retardance scan 901 includes two regions in the sample that was scanned: a region 951 that corresponds to the portion 931 of the OCT A-line intensity scan 902 above the threshold intensity, and a region 952 that that corresponds to a portion of the OCT A-line intensity scan 902 below the threshold intensity. The two regions 951, 952 are delineated in FIG. 9 via a line 960 drawn from the edge of the portion 931 opposite an edge adjacent the sample surface (as indicated by the line 910). As the region 952 is a region where accurate OCT measurements may no longer be possible, the region 952 may be ignored.

As depicted, the region 951 includes bands due to tissue organization in the sample from which the PSOCT A-line retardance scan 901 was obtained. In particular, the region 951 includes five bands, with a band closest to the line 910 representing tissue organization of the sample closest to the surface of the sample, and a band closest to the line 960 representing tissue organization of the sample at a deepest measurable location in the sample. Indeed, each of the bands in the region 951 may be indicative of tissue organization at different respective depths in the sample. When the bands in the region 951 are all similar, the tissue organization may be similar throughout the measurable depth of the sample; and when one or more bands in the region 951 are different from other bands in the regions 951, the tissue organization may be changing throughout the measurable depth of the sample.

As depicted, bands in the PSOCT A-line retardance scan 901 have been identified by the computing device 620 at the block 706 by identifying the region 951, at least in part, based on the intensity threshold, represented by the line 930, applied to corresponding OCT A-line intensity scan 902, as well as the segmentation, represented by the line 910. Alternatively, and/or in addition to, the bands in the in the PSOCT A-line retardance scan 901 may be identified using signal analysis techniques, for example by "looking" for regions of the OCT A-line intensity scan 902 that meet criteria that define bands, such criteria may define a shape of bands, regularity, and the like.

As depicted a rising slope of the first band in the region 951, as indicated by the line 970, has being determined by the computing device 620 at the block 708. In other words, in the depicted embodiment, the frequency characteristic is a rising slope of the first band in the region 951. Alternatively, a falling slope of the first band in the region 951 may be determined.

However, rising or falling slopes of any of the other bands may be determined. In some embodiments, the average of the rising and/or falling slopes of two or more of the bands may be determined. For example, attention is directed to FIG. 10 which also depicts the PSOCT A-line retardance scan 901, however in FIG. 10, the computing device 620 has determined the rising slope of each of the first band, the second band and the third band, as respectively represented by the lines 970, 1070, 1080.

In yet further embodiments, a rising or falling slope of bands at a given depth and/or range of depths, may be determined. For example, each successive band represents tissue organization at successive depths in the sample; hence, when an indication of tissue organization at a given depth and/or range of depths is to be determined, rising or falling slopes of one or more bands at the given depth may be determined; when rising or falling slopes of two or more bands are determined in a range, an average of the rising or falling slopes of the two or more bands in the range are determined.

Hence, in these embodiments, the frequency characteristic of the bands in the region 951 determined at the block 708 comprises a rising or falling slope of one or more of the bands and/or an average thereof.

Alternatively, the frequency characteristic of the bands in the region 951 determined at the block 708 may comprise a rising or falling slope multiplied by a number of the bands used to determine the slope.

In addition, while only one PSOCT A-line retardance line scan 901 is depicted herein, showing five bands, PSOCT A-line retardance line scan in other regions of the sample may include no bands, indicating an absence of tissue organization, fewer than five bands, indicating less tissue organization, or more than five bands, indicating more tissue organization. Furthermore, a frequency characteristic of any bands may change as the tissue organization changes; for example, in the example of the frequency characteristic comprising a rising or falling slope of one or more bands, such slopes may increase or decrease depending on the tissue organization and/or the number of bands. When there are no bands in a PSOCT A-line retardance line scan, the computing device 620 may be configured to set a frequency characteristic to a default "no tissue organization value", such as "0".

Figure 11:
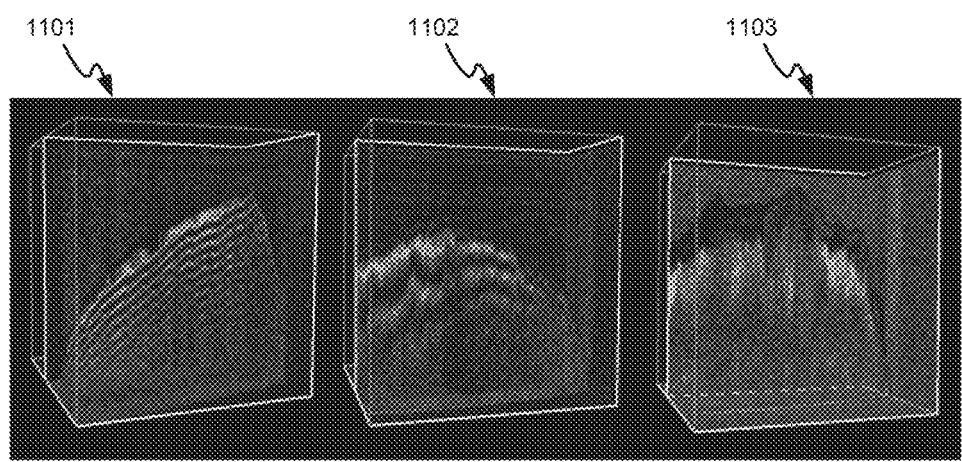
FIG. 11 depicts three three-dimensional PSOCT retardance scans of samples with decreasing tissue organization, according to non-limiting implementations.

For example, attention is directed to FIG. 11 which depicts three three-dimensional PSOCT retardance scans 1101, 1102, 1103 of samples with decreasing tissue organization. In the scan 1101, there are about seven bands, indicating high tissue organization; in the scan 1102, there about three bands, each broader than the bands of the scan 1101, indicating less tissue organization as compared to the scan 1101; and in the in the scan 1103, there is one band, broader than the bands of the scan 1102, indicating less tissue organization as compared to the scan 1102.

Furthermore, as indicated above, when the tissue organization is depth dependent, the bands may be distributed across PSOCT A-line retardance line scan 901 in a manner that is dependent on the depth dependency of the tissue organization. For example, when there is tissue organization only at a surface, there may be one "sharp" band in a PSOCT A-line retardance line scan in a region corresponding to the surface (e.g. as similar to the bands of the scan 1101), and the remaining portion of the PSOCT A-line retardance line scan may include no bands.

Figure 12:
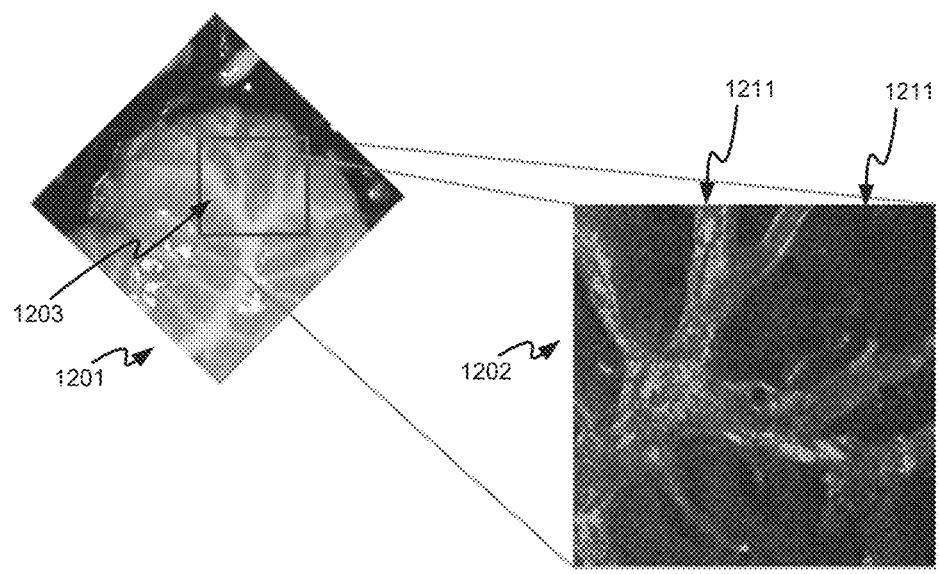
FIG. 12 depicts an image of a sample, and a map of frequency characteristic of the sample, according to non-limiting implementations.

Attention is next directed to FIG. 12 which depicts an example embodiment of the block 710 of the method 700. In particular, FIG. 12 depicts an image 1201 of the sample 630, and a map 1202 of the frequency characteristic. The image 1201 may comprise an en-face image acquired by the PSOCT device 601, or an image acquired by a camera device. It is assumed in FIG. 12 that the computing device 620 has generated the map 1202 from PSOCT A-line scans across an area 1203 of the sample 630. Put another way, the PSOCT device 601 was controlled by the computing device 620 to perform a plurality of PSOCT B-line scans occurred across the area 1203.

It is furthermore assumed in FIG. 12 that the map 1202 is being rendered at the display device 603, for example by the computing device 620 at the block 710 of the method 700.

As depicted, the map 1202 may comprise a false color map, and the like of the area 1203, the map 1202 comprising two types of regions: lighter regions 1211 showing where there is high tissue organization (and e.g. the rising or falling slope of the bands is large) and darker regions 1211 where there is low or no tissue organization (and e.g. the rising or falling slope of the bands is low and/or set to a default value). Indeed, different values and/or ranges of the frequency characteristic may be assigned a different color and/or gray scale value and rendered on the map 1202 according to a location of the area 1203 where a corresponding PSOCT A-line scan occurred. Hence, a surgeon, and the like, may view the map 1202 and visually determine where different regions of tissue organization are present in the sample 630, and perform surgery accordingly.

In some embodiments, the computing device 520 may control the PSOCT device 601 to obtain one or more of an image and an en-face image of the sample 630 and control the display device 603 to render the map 1202 of the frequency characteristic on one or more of the image and the en-face image. Put another way, the map 1202 may be rendered and/or overlaid on the image 1201, assuming that the regions of the map 1202 may be aligned with corresponding regions of the image 1201. Furthermore, rectification of the map 1202 onto the image 1201 (or vice versa) may may be performed to render and/or overlay the data of each of the map 1202 and the image 1201 together.

Heretofore, the frequency characteristic, determined at the block 708 of the method 700, has been discussed with respect to a slope of bands. However, the frequency characteristic may be determined using various transforms of PSOCT A-line retardance scans including, but not limited to, Fourier Transforms. In some of these implementations segmentation at the block 704 and/or band identification at the block 706 may not occur in the method 700.

Attention is next directed to FIG. 13 to FIG. 19, each of which depict Fourier Transforms performed on the PSOCT A-line retardance scan 901 by the computing device 620, and/or windows thereof.

Figure 13:
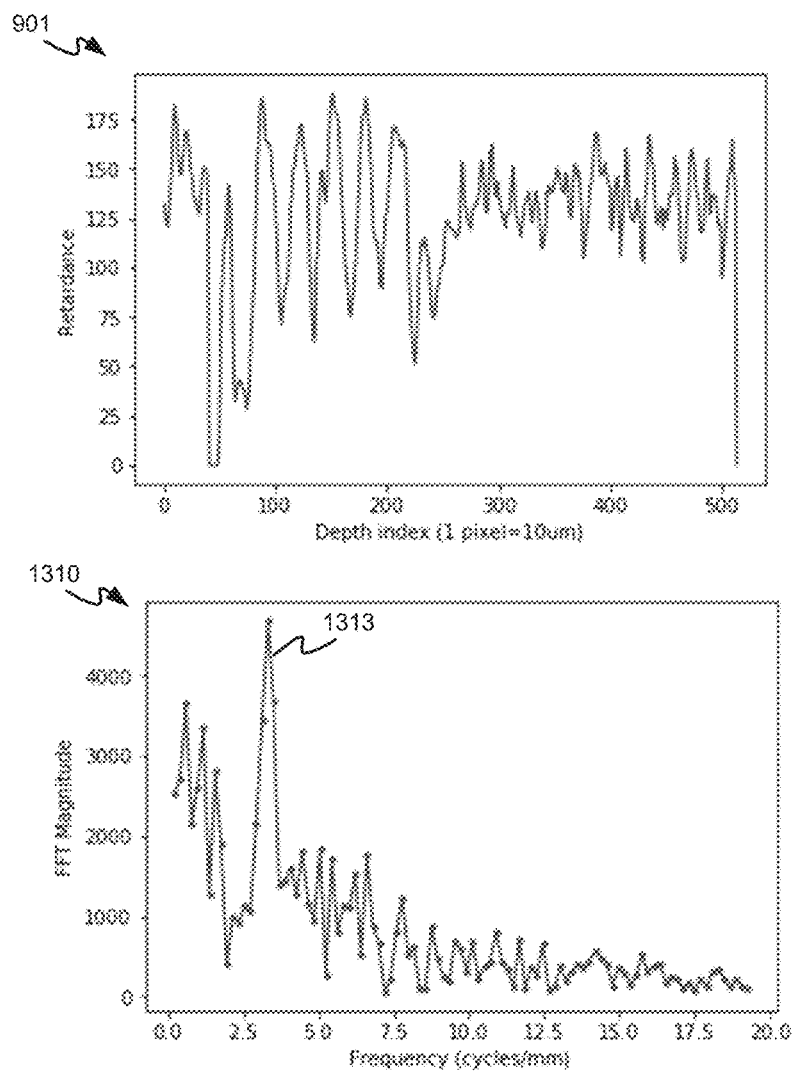
FIG. 13 depicts an PSOCT A-line retardance and a Fourier Transform of the PSOCT A-line retardance scan without segmentation and without explicit band identification, according to non-limiting implementations.

For example, FIG. 13 depicts the PSOCT A-line retardance scan 901 (also showing that the depth index of the x-axis is in units of pixels with 1 pixel per 10 microns, and over 514 pixels and/or points) and a Fourier Transform 1310 of the PSOCT A-line retardance scan 901 without segmentation and without explicit band identification. A dominant frequency 1313 occurs at a frequency corresponding to about 3.3 cycles/mm (which may optionally be converted to frequency in Hz, and the like) and/or between 3 to 3.5 cycles/mm (e.g. 3.3 cycles/mm being at about a center of the frequency 1313). Hence, in these embodiments, the frequency characteristic for the PSOCT A-line retardance scan 901 is 3.3 cycles/mm.

While not depicted, the frequency characteristic for the PSOCT A-line retardance scan 901 may alternatively comprise a Fourier Transform coefficient of the dominant frequency 1413 of the Fourier Transform of the respective PSOCT A-line retardance scan 901 and/or the bands of the respective PSOCT A-line retardance scan 901, the Fourier Transform coefficient of the dominant frequency 1413 being a highest Fourier Transform coefficient of a plurality of Fourier Transform coefficients. In other words, the Fourier Transform 1310 may be expressed numerically as function of frequencies and corresponding coefficients, and the frequency characteristic for the PSOCT A-line retardance scan 901 may comprise the largest of these coefficients.

Figure 14:
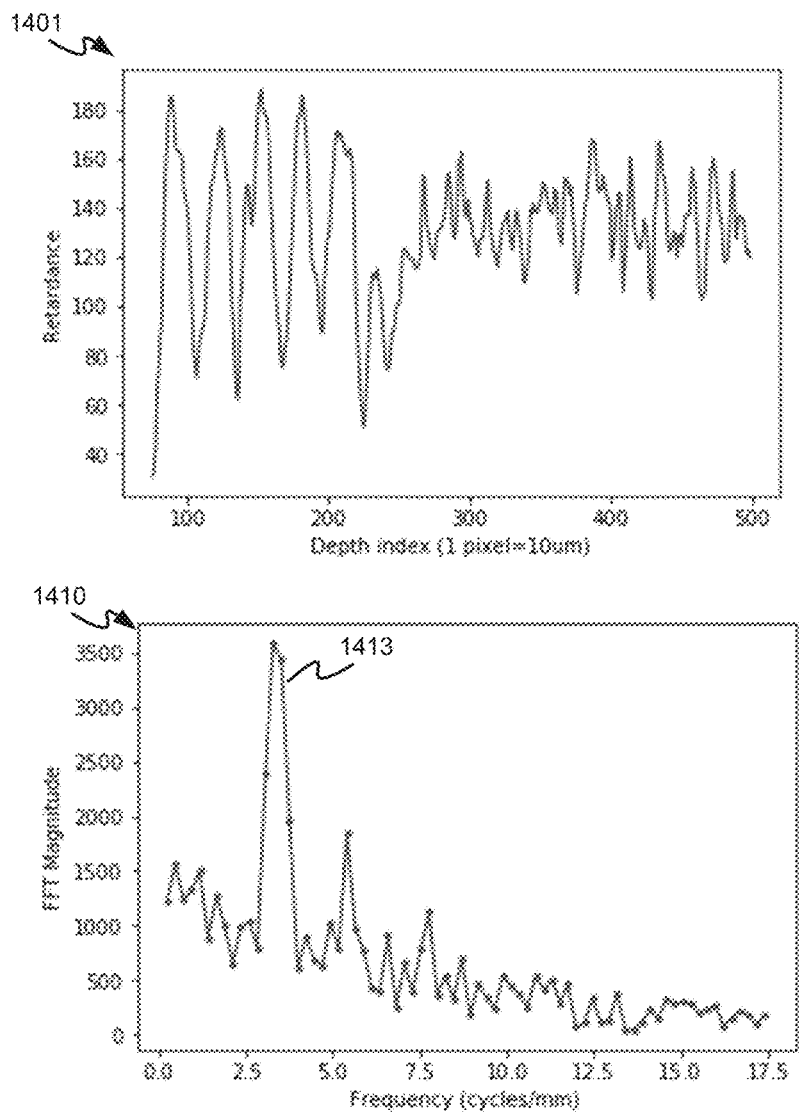
FIG. 14 depicts the PSOCT A-line retardance of FIG. 13 with segmentation and a Fourier Transform of the PSOCT A-line retardance scan in a window of the PSOCT A-line retardance scan that starts at the tissue surface, according to non-limiting implementations.

FIG. 14 is similar to FIG. 13, however, in FIG. 14 segmentation has occurred and the computing device 620 has performed a Fourier Transforms on a window 1401 of the PSOCT A-line retardance scan 901 that starts at the tissue surface (i.e. starting at a depth index of 75, which delineates the start of the region 951, and the region 952, to a depth index of 500). However, the resulting Fourier Transform 1410 results in a dominant frequency 1413 similar to the dominant frequency 1313 determined without segmentation. Hence, in these embodiments, segmentation to determine the window 1401 that includes only that portion of PSOCT A-line retardance scan 901 that is in the sample may be superfluous.

Figure 15:
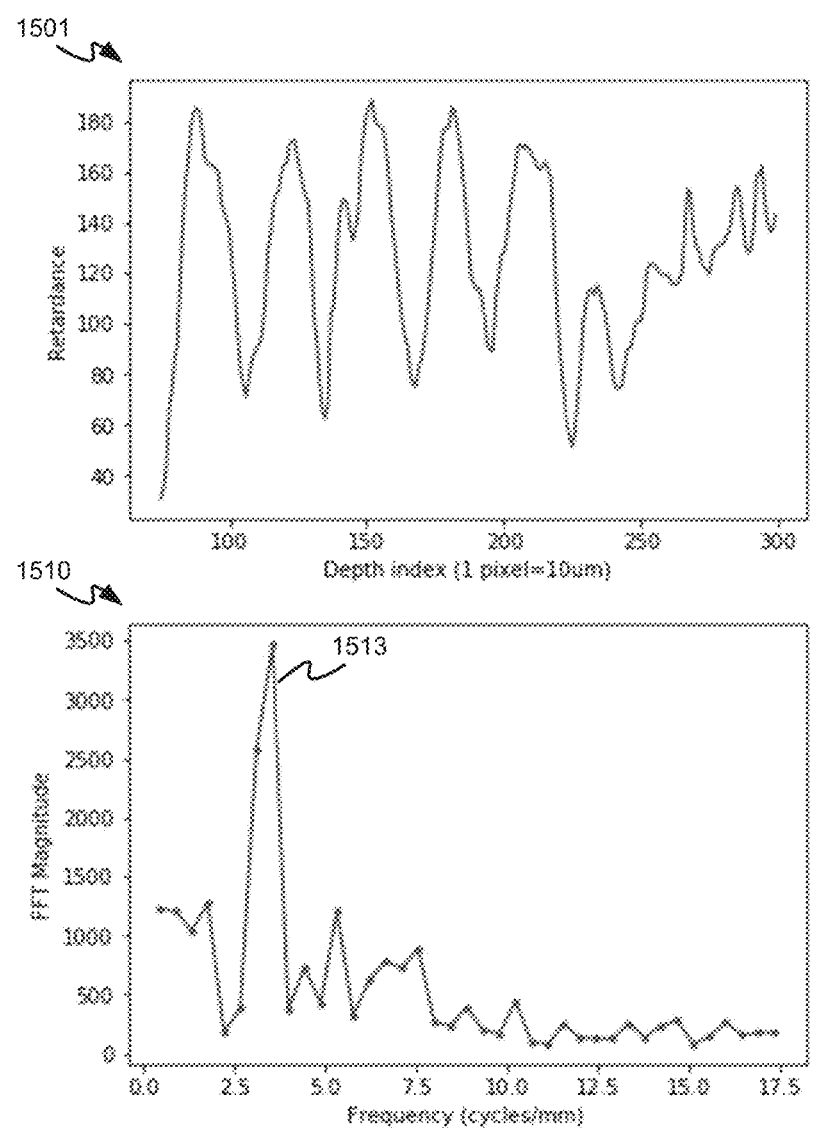
FIG. 15 depicts the PSOCT A-line retardance of FIG. 13 with segmentation and a Fourier Transform of the PSOCT A-line retardance scan in a window of the PSOCT A-line retardance scan that starts at the tissue surface and ends in a region below a threshold intensity, according to non-limiting implementations.

FIG. 15 is similar to FIG. 14, however, in FIG. 15 the computing device 620 has performed a Fourier Transforms on a window 1501 of the PSOCT A-line retardance scan 901 that starts at the tissue surface (e.g. at a depth index of 75 at the region 951) and ends partly into the region 952 (e.g. at a depth index of 300). However, the resulting Fourier Transform 1510 results in a dominant frequency 1513 similar to the dominant frequencies 1313, 1413. Hence, in these embodiments, segmentation and reducing the size of the window 1501, as compared to the window 1401, may be superfluous.

Figure 16:
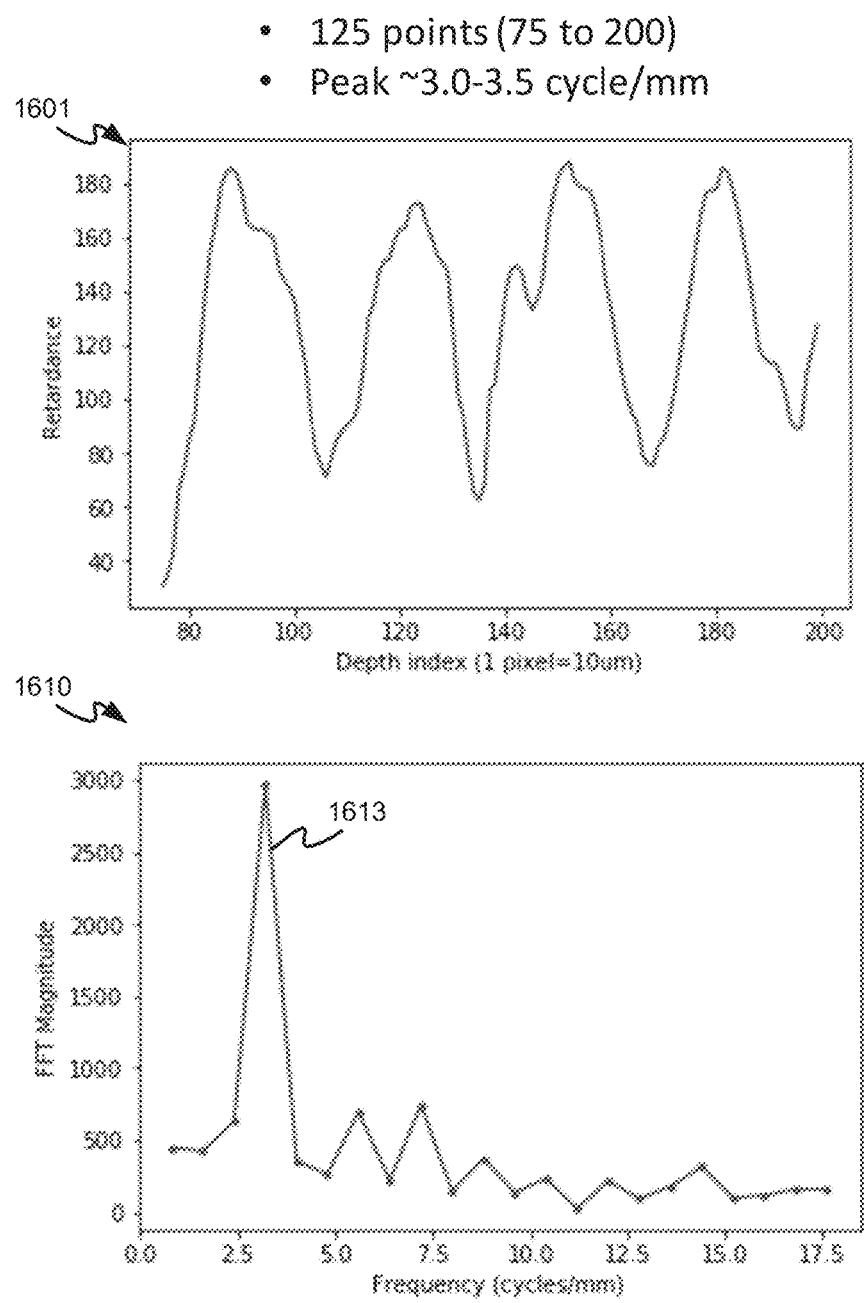
FIG. 16 depicts the PSOCT A-line retardance of FIG. 13 with segmentation and a Fourier Transform of the PSOCT A-line retardance scan in a window of the PSOCT A-line retardance scan that starts at the tissue surface and ends in a region above a threshold intensity, according to non-limiting implementations.

FIG. 16 is similar to FIG. 15, however, in FIG. 16 segmentation has occurred and the computing device 620 performs a Fourier Transforms performed on a window 1601 of the PSOCT A-line retardance scan 901 that includes only a portion of the region 951 (e.g. from a depth index of 75 to a depth index of 200). Hence, the window 1601 for which the Fourier Transform 1610 is performed excludes the deepest part of the region 951. However, the resulting Fourier Transform 1610 results in a dominant frequency 1613 similar to the dominant frequencies 1313, 1413, 1513.

Figure 17:
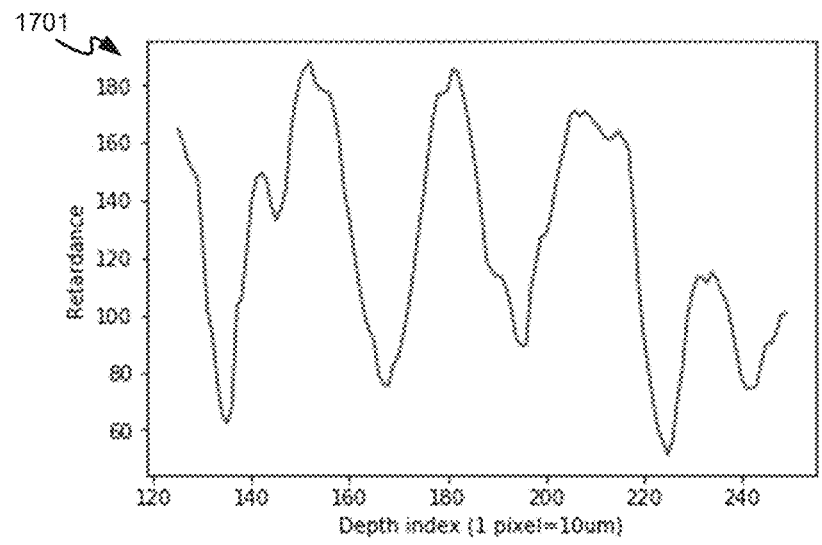
FIG. 17 depicts the PSOCT A-line retardance of FIG. 13 with segmentation and a Fourier Transform of the PSOCT A-line retardance scan in a window the same size as the window of FIG. 16, but shifted deeper into the sample, according to non-limiting implementations.
Figure 17:
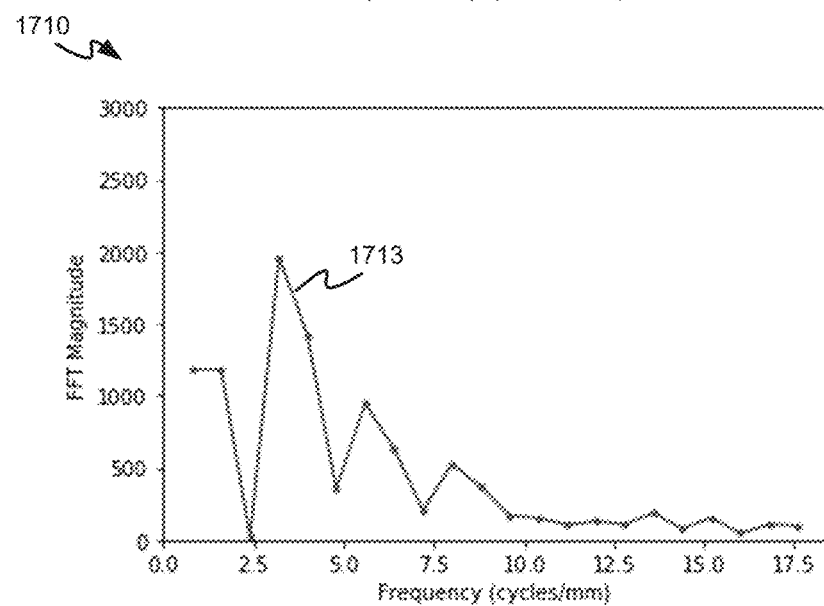

Attention is next directed to FIG. 17 in which the computing device 620 performs a Fourier Transforms performed on a window 1701 that is a same size as the window 1601, but shifted deeper into the sample (e.g. from a depth index of 125 to a depth index of 250). However, the resulting Fourier Transform 1710 results in a dominant frequency 1713 similar to the dominant frequencies 1313, 1413, 1513, 1613. Hence, comparing FIG. 17 to FIG. 16, it appears that the tissue organization is similar throughout the depth of the sample. However, it is noted that the dominant frequency 1713 has a different shape than the dominant frequency 1613; hence, a respective highest Fourier Transform coefficient may be different for each of the dominant frequencies 1613, 1713.

Figure 18:
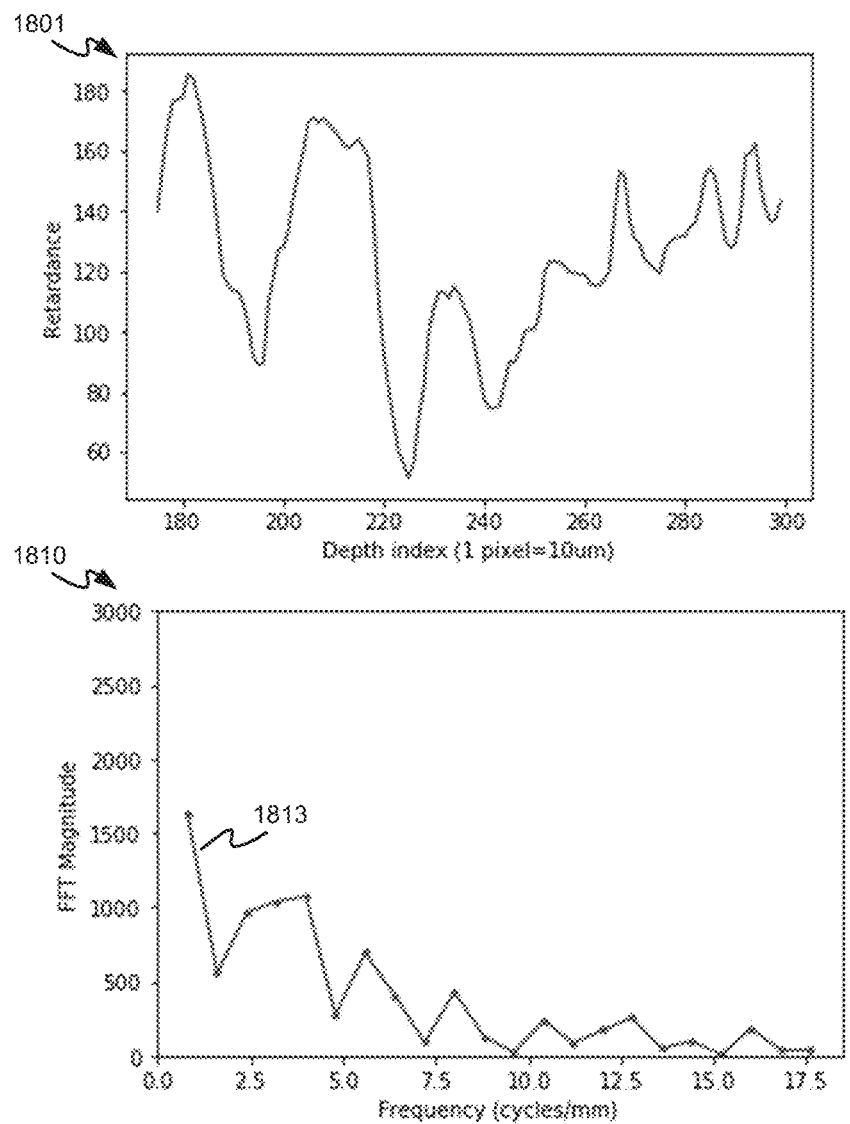
FIG. 18 depicts the PSOCT A-line retardance of FIG. 13 with segmentation and a Fourier Transform of the PSOCT A-line retardance scan in a window the same size as the window of FIG. 17, but shifted yet deeper into the sample, according to non-limiting implementations.

Attention is next directed to FIG. 18 in which the computing device 620 performs a Fourier Transforms performed on a window 1801 that is a same size as the window 1701, but shifted deeper into the sample (e.g. from a depth index of 175 to a depth index of 300) and includes only the two deepest peaks of the region 951, and a portion of the region 952. However, the resulting Fourier Transform 1810 results in a dominant frequency 1813 that is no longer similar to the dominant frequencies 1313, 1413, 1513, 1613, 1713. Hence, comparing FIG. 18 to FIG. 17, it appears that the tissue organization may be similar throughout the depth of the sample other than close to depths where OCT scanning is no longer possible, i.e. at depths corresponding to the two deepest peaks.

Figure 19:
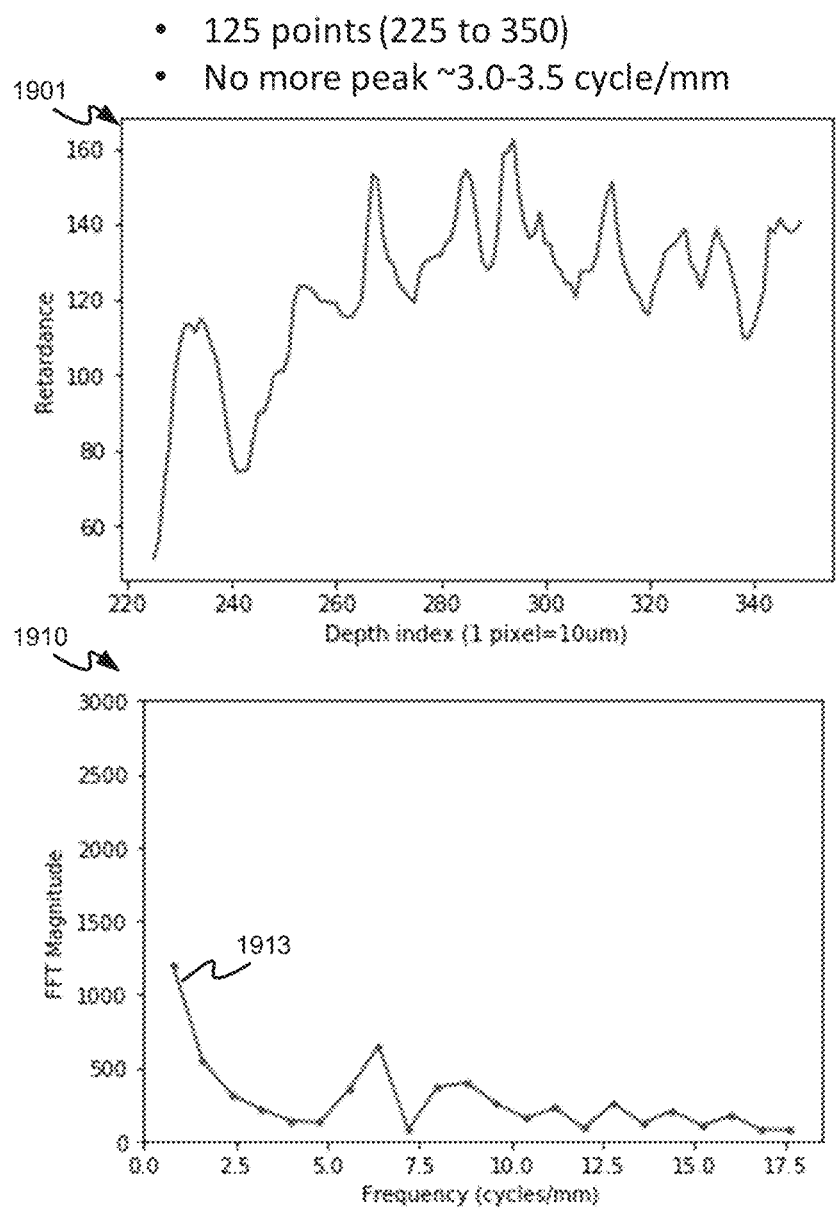
FIG. 19 depicts the PSOCT A-line retardance of FIG. 13 with segmentation and a Fourier Transform of the PSOCT A-line retardance scan in a window the same size as the window of FIG. 18, but again shifted yet deeper into the sample as compared to the window of FIG. 17, according to non-limiting implementations.

Attention is next directed to FIG. 19 in which the computing device 620 performs a Fourier Transforms performed on a window 1901 that is a same size as the window 1801, but shifted deeper into the sample (e.g. from a depth index of 235 to a depth index of 350) and includes only the deepest peak of the region 951, and a portion of the region 952. The resulting Fourier Transform 1910 results in a dominant frequency 1913 that is again longer similar to the dominant frequencies 1313, 1413, 1513, 1613, 1713 but may be similar to the dominant frequency 1813. Hence, comparing FIG. 19 to FIG. 17, FIG. 19 again shows that the tissue organization may be similar throughout the depth of the sample other than close to depths where OCT scanning is no longer possible, i.e. at a depth corresponding to the deepest peak.

Comparing the FIG. 16, FIG. 17, FIG. 18 and FIG. 19, a sliding window may be used to determine frequency characteristics of a PSOCT A-line retardance scan at different depth ranges. Similarly, comparing FIG. 13, FIG. 14, FIG. 15 and FIG. 16, a window may be widened or narrowed to determine frequency characteristics over different sizes of depth ranges. Each technique may result in a corresponding map that may be useful to a surgeon.

Indeed, the computing device 620 may determine the frequency characteristic as function of depth in the sample, and the computing device 620 may be further configured to: control the display device 603 to render a map of the frequency characteristic according to the depth. Alternatively, the computing device 620 may be configured to control the display device 603 to render a map of the frequency characteristic according to depth. Indeed, the computing device 620 may control the display device 603 to render more than one map of the frequency characteristic at different depths.

The depth may be selected based on input received at the computing device 620 and/or adjusted "on the fly" during surgery, to show tissue organization at different depths in the sample. Indeed, where changes in the frequency characteristic are "abrupt" and/or inhomogeneous, according to depth (e.g. the frequency characteristic as a function of depth may be similar to a step function), such adjustment of the depth of the map highlight such inhomogeneities.

Alternatively, the computing device 620 may be configured to identify inhomogeneities in the sample as a function of the depth for example based on abrupt changes in banding, as determined using the slopes, and/or when there is more than one dominant frequency in a Fourier Transform of the PSOCT retardance scan. For example, the computing device 620 may control the display device 603 to provide an alert of such inhomogeneities in the sample, and/or regions of such inhomogeneities, as they may not be easy to visually discern in a map that shows the frequency characteristic at one depth.

Furthermore, while FIG. 13 to FIG. 19 are described with respect to determining a frequency characteristic of a dominant Fourier Transform frequency, in other embodiments a frequency characteristic may be determined using a wavelet transform. For example, in these embodiments, the frequency characteristic determined by the computing device 620 may comprise a dominant frequency determined from a wavelet transform of a respective PSOCT A-line retardance scan. For example, at such embodiments, a wavelet transform will result in a maximum power at a dominant frequency, which may also characterize the tissue organization.

Hence, provided herein is a system and method for characterizing tissue organization using polarization sensitive optical coherence tomography in which a frequency characteristic of bands of PSOCT A-line retardance scans are determined over an area of sample. The frequency characteristic is mapped at a display device to show how the tissue organization differs across the area of the sample. The depth at which the frequency characteristic is determined may be adjusted to show tissue organization at different depths. The techniques described herein are non-invasive and may be performed in-vivo or in-vitro.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A system comprising:
a polarization sensitive optical coherence tomography (PSOCT) device;
a display device; and
a computing device configured to:
control the PSOCT device to obtain PSOCT A-line scans across a sample;
for each of the PSOCT A-line scans, determine a frequency characteristic of any banding present in a respective PSOCT A-line retardance scan; and
control the display device to render a map of the frequency characteristic.

2. The system of claim 1, wherein the frequency characteristic comprises one of: a rising slope of a band in the respective PSOCT A-line retardance scan; a falling slope of the band in the respective PSOCT A-line retardance scan; an average of rising slopes of two or more bands in the respective PSOCT A-line retardance scan; an average of fallings slopes of the two or more bands in the respective PSOCT A-line retardance scan; and an average of a of the rising slopes and the falling slopes of the two or more bands in the respective PSOCT A-line retardance scan.

3. The system of claim 1, wherein the frequency characteristic comprises a slope of one or more of bands in the respective PSOCT A-line retardance scan multiplied by a number of the bands used to determine the slope.

4. The system of claim 1, wherein the frequency characteristic comprises one of: a dominant frequency determined from a Fourier Transform of the respective PSOCT A-line retardance scan; and a Fourier Transform coefficient of the dominant frequency of the Fourier Transform of the respective PSOCT A-line retardance scan, the Fourier Transform coefficient of the dominant frequency being a highest Fourier Transform coefficient of a plurality of Fourier Transform coefficients.

5. The system of claim 1, wherein the frequency characteristic comprises: a dominant frequency determined from a wavelet transform of the respective PSOCT A-line retardance scan.

6. The system of claim 1, wherein the frequency characteristic is determined as a function of depth in the sample, and the computing device is further configured to: control the display device to render the map of the frequency characteristic according to the depth.

7. The system of claim 6 wherein the computing device is further configured to identify inhomogeneities in the sample as a function of the depth.

8. The system of claim 1, wherein the computing device is further configured to: identify bands of each of the PSOCT A-line retardance scans based on one or more of: an intensity threshold applied to corresponding PSOCT A-line intensity scans; and signal analysis techniques.

9. The system of claim 1, wherein the computing device is further configured to:
control the PSOCT device to obtain one or more of an image and an en-face image of the sample; and
control the display device to render the map of the frequency characteristic on one or more of the image and the en-face image.

10. The system of claim 1, wherein the computing device is further configured to: perform segmentation on an image of the sample, prior to determining the frequency characteristic of any banding present in the respective PSOCT A-line retardance scan, determine a region of the PSOCT A-line scans that includes a tissue signal.

11. A method comprising:
controlling, at a computing device, a polarization sensitive optical coherence tomography (PSOCT) device to obtain PSOCT A-line scans across a sample;
for each of the PSOCT A-line scans, determining, at the computing device, a frequency characteristic of any banding present in a respective PSOCT A-line retardance scan; and
controlling, at a computing device, a display device to render a map of the frequency characteristic.

12. The method of claim 11, wherein the frequency characteristic comprises one of: a rising slope of a band in the respective PSOCT A-line retardance scan; a falling slope of the band in the respective PSOCT A-line retardance scan; an average of rising slopes of two or more bands in the respective PSOCT A-line retardance scan; an average of fallings slopes of the two or more bands in the respective PSOCT A-line retardance scan; and an average of a of the rising slopes and the falling slopes of the two or more bands in the respective PSOCT A-line retardance scan.

13. The method of claim 11, wherein the frequency characteristic comprises a slope of one or more of bands in the respective PSOCT A-line retardance scan multiplied by a number of the bands used to determine the slope.

14. The method of claim 11, wherein the frequency characteristic comprises one of: a dominant frequency determined from a Fourier Transform of the respective PSOCT A-line retardance scan; and a Fourier Transform coefficient of the dominant frequency of the Fourier Transform of the respective PSOCT A-line retardance scan, the Fourier Transform coefficient of the dominant frequency being a highest Fourier Transform coefficient of a plurality of Fourier Transform coefficients.

15. The method of claim 11, wherein the frequency characteristic comprises: a dominant frequency determined from a wavelet transform of the respective PSOCT A-line retardance scan.

16. The method of claim 11, wherein the frequency characteristic is determined as a function of depth in the sample, and the method further comprises: controlling, at the computing device, the display device to render the map of the frequency characteristic according to the depth.

17. The method of claim 16, further comprising identifying, at the computing device, inhomogeneities in the sample as a function of the depth.

18. The method of claim 11, further comprising identifying, at the computing device, bands of each of the PSOCT A-line retardance scans based on one or more of: an intensity threshold applied to corresponding PSOCT A-line intensity scans; and signal analysis techniques.

19. The method of claim 11, further comprising:
controlling, at the computing device, the PSOCT device to obtain one or more of an image and an en-face image of the sample; and
controlling, at the computing device, the display device to render the map of the frequency characteristic on one or more of the image and the en-face image.

20. The method of claim 11, further comprising: performing segmentation on an image of the sample, prior to determining the frequency characteristic of any banding present in the respective PSOCT A-line retardance scan, determine a region of the PSOCT A-line scans that includes a tissue signal.

* * * * *